(12) United States Patent
Styring et al.

(10) Patent No.: US 6,184,322 B1
(45) Date of Patent: Feb. 6, 2001

(54) METAL-CONTAINING SIDE CHAIN LIQUID CRYSTAL POLYMERS

(75) Inventors: Peter Styring; Isabel M. Saez; Neil Gough; Ekkehard Sinn; John W Goodby, all of Hull (GB)

(73) Assignee: The Secretary of State for Defence in Her Britannic Majesty's Government of the United Kingdom of Great Britain and Northern Ireland, Farnborough (GB)

( * ) Notice: Under 35 U.S.C. 154(b), the term of this patent shall be extended for 0 days.

(21) Appl. No.: 09/194,778

(22) PCT Filed: Jun. 12, 1997

(86) PCT No.: PCT/GB97/01584

§ 371 Date: Dec. 3, 1998

§ 102(e) Date: Dec. 3, 1998

(87) PCT Pub. No.: WO97/49671

PCT Pub. Date: Dec. 31, 1997

(30) Foreign Application Priority Data

Jun. 21, 1996 (GB) .................................................. 9613068

(51) Int. Cl.[7] .......................... C09K 19/40; C08F 30/04; C08F 283/13; C08G 33/04; C07F 7/10

(52) U.S. Cl. ............... 526/241; 252/299.61; 252/299.62; 525/475; 528/30; 528/31; 556/406

(58) Field of Search ........................ 252/299.61, 299.62; 556/406; 526/241; 525/475; 528/30, 33

(56) References Cited

FOREIGN PATENT DOCUMENTS

242278 * 10/1987 (EP) .

OTHER PUBLICATIONS

CAPLUS 1990: 632164.
Oriol L et al: "Metallomesogenic Polymers" Advanced Materials, vol. 7, No. 4, Apr. 1, 1995, pp. 348–369, XP000502862 see pp. 355–357, paragraph 5.1.1.
J.S. Moore: "Paramagnetic organometallic liquid crystal polymers" Polymer Bulletin., vol. 19, 1988, Heidelberg DE, pp. 251–256, XP002040771 see the whole document.
Saez I M et al: "Oligo(siloxane) rings and cages possessing nickel–containing liquid crystal side chains" Asv. Mater. (Weinheim, Ger.) (ASVMEW,093595648);96; vol. 8 (12); pp. 1001–1005, University Hull;School Chemistry; Hull; HU6 7RX; UK (GB), XP000637936 see the whole document.

* cited by examiner

*Primary Examiner*—Shean C. Wu
(74) *Attorney, Agent, or Firm*—Nixon & Vanderhye

(57) ABSTRACT

A group fo liquid crystalline compounds defined by formulas (1) and (2)

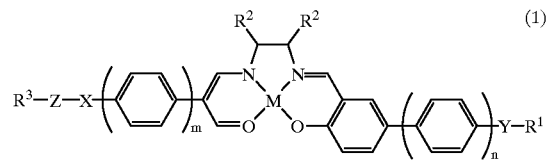

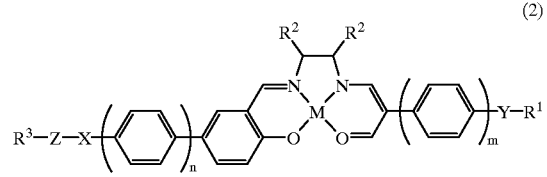

including polymers, monomers, oligomers and intermediates for their preparation. Also included are symmetric and non-symmetric poly(dimethylsiloxy) compounds having end groups derived from Formulas (1) and (2).

14 Claims, 14 Drawing Sheets

Fig. 1.
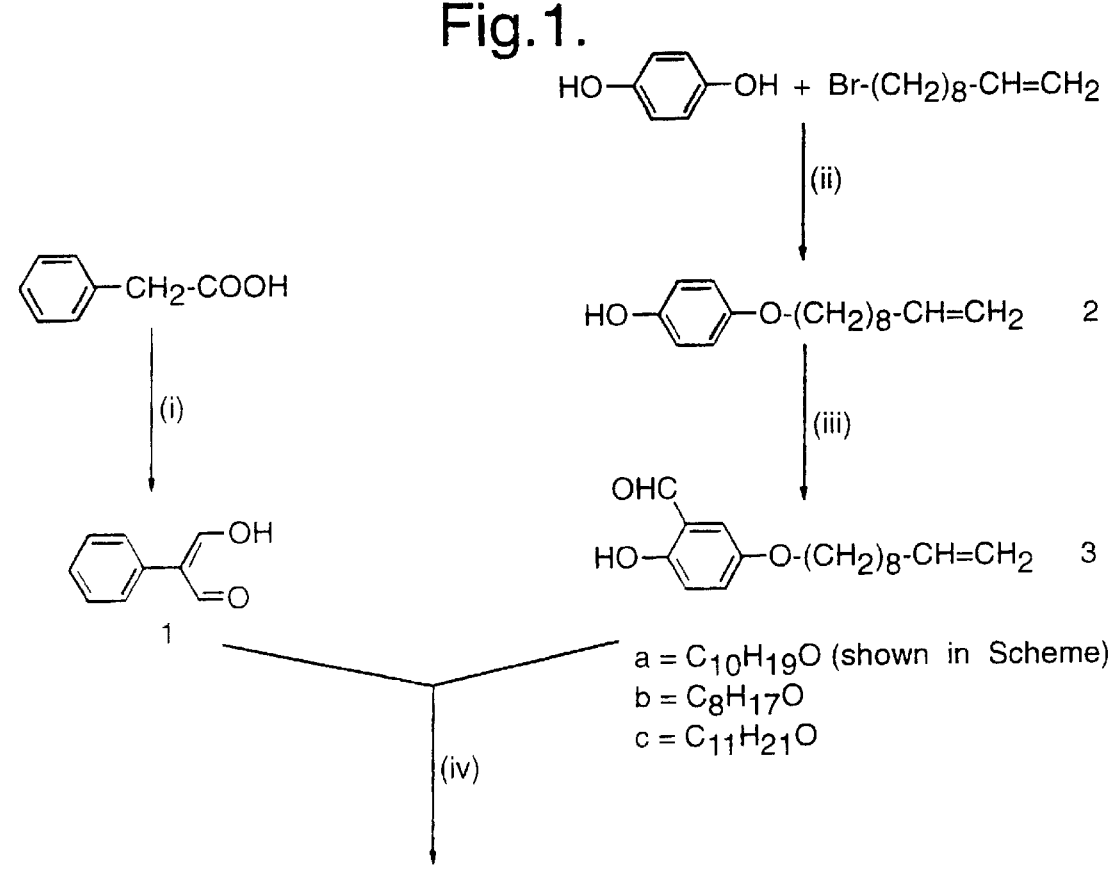
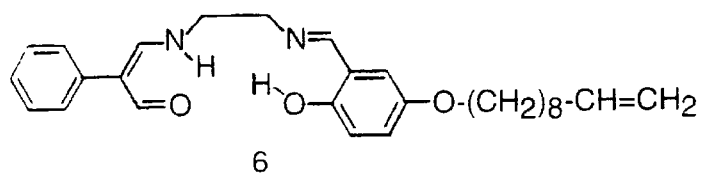
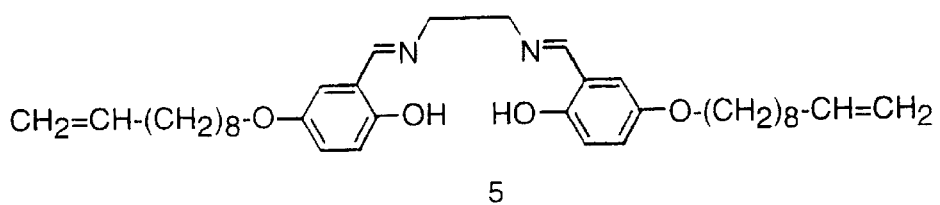
(i) (a) POCl$_3$/DMF, (b) NaOH, (c) HCl; (ii) KOH;
(iii) (HCHO)$_n$/SnCl$_4$/Bu$^n_3$N; (iv) H$_2$NCH$_2$CH$_2$NH$_2$

Fig. 3.
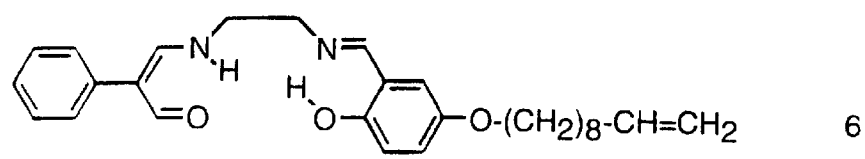
6
↓ (i)
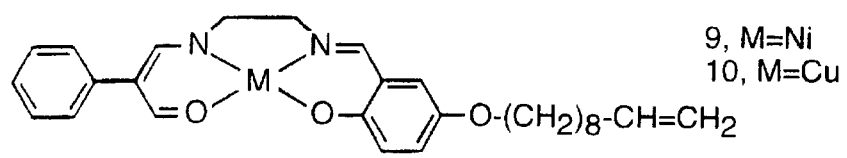
9, M=Ni
10, M=Cu
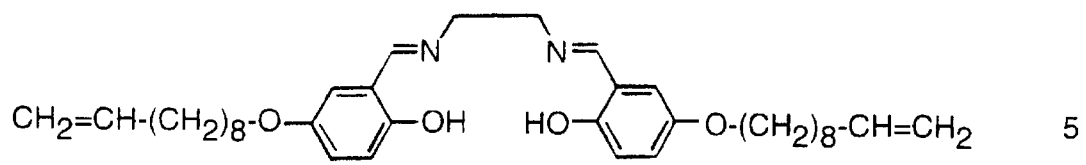
5
↓ (I)
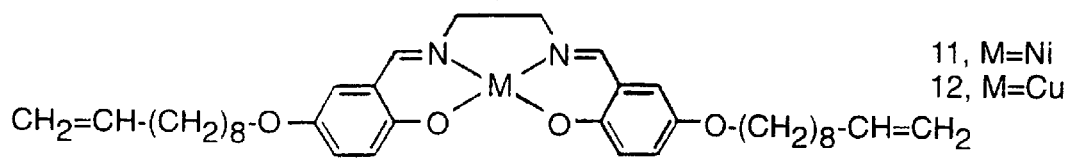
11, M=Ni
12, M=Cu
(i) [M(AcO)₂]

Fig.4.
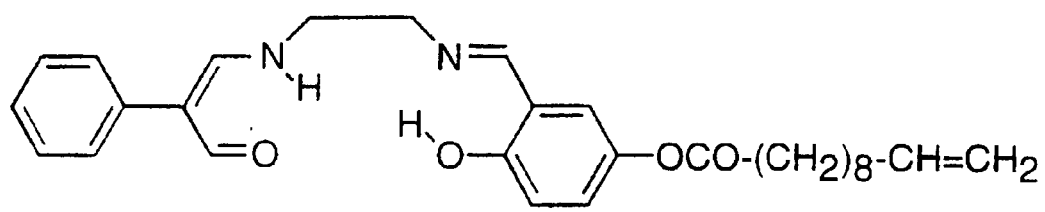
8
↓ (i)
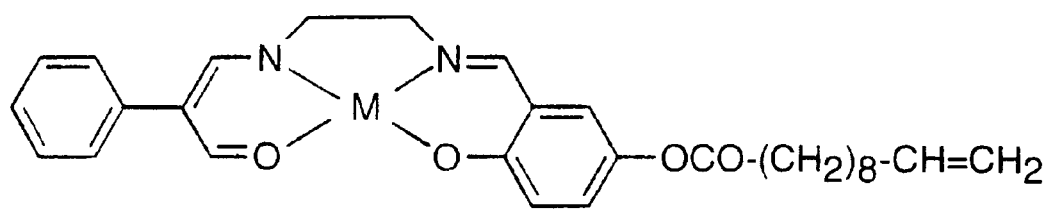
13, M=Ni
14, M=Cu
15, M=VO
(i) [M(OAc)$_2$]

(i) $K_2CO_3$, butanone, reflux; (ii) NaOH (25%), $C_2H_5OH$,
(iii) $POCl_3$, DMF, 70°C, 20 h; (iv) (a) NaOH, (b) HCl

Fig. 9.
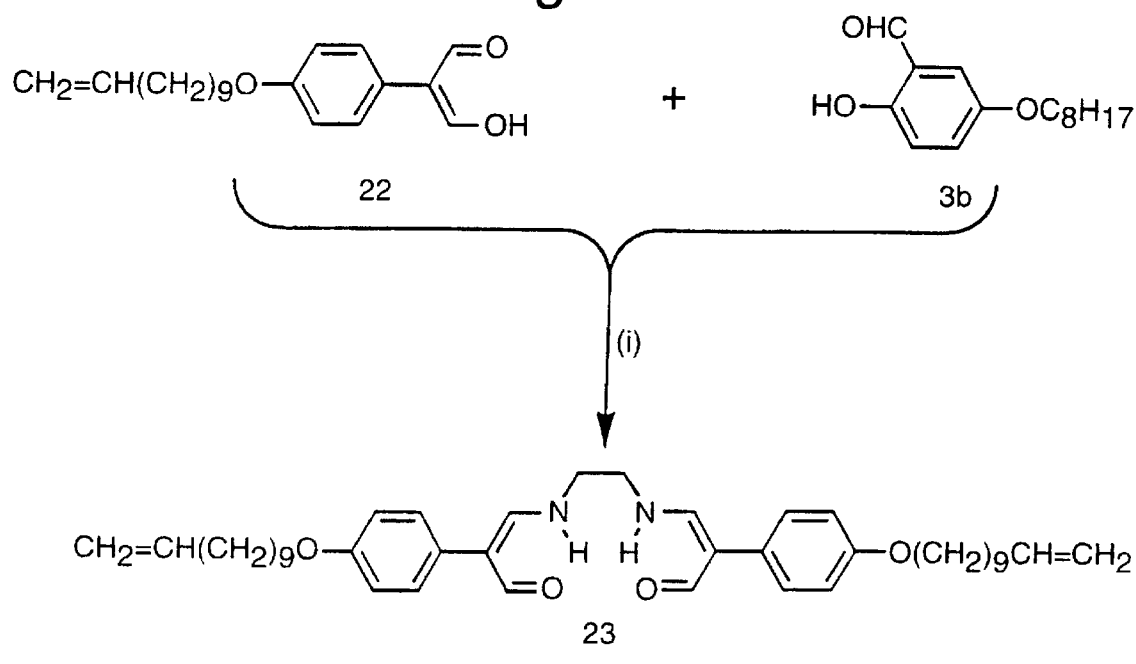
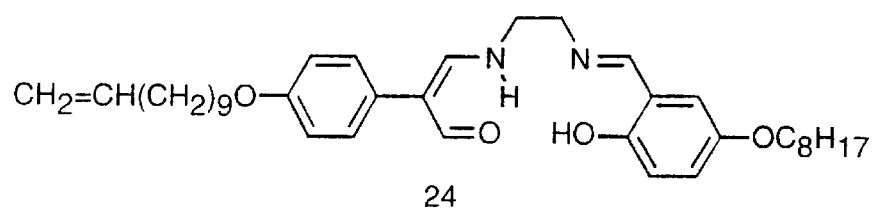
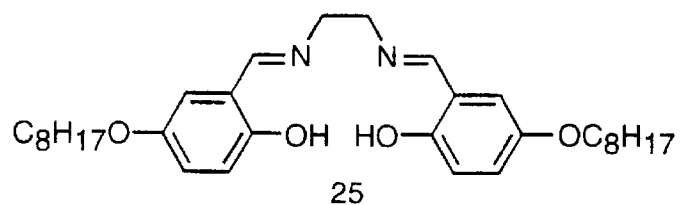
(i) 1,2-diaminoethane / CH₂Cl₂

Fig. 11.
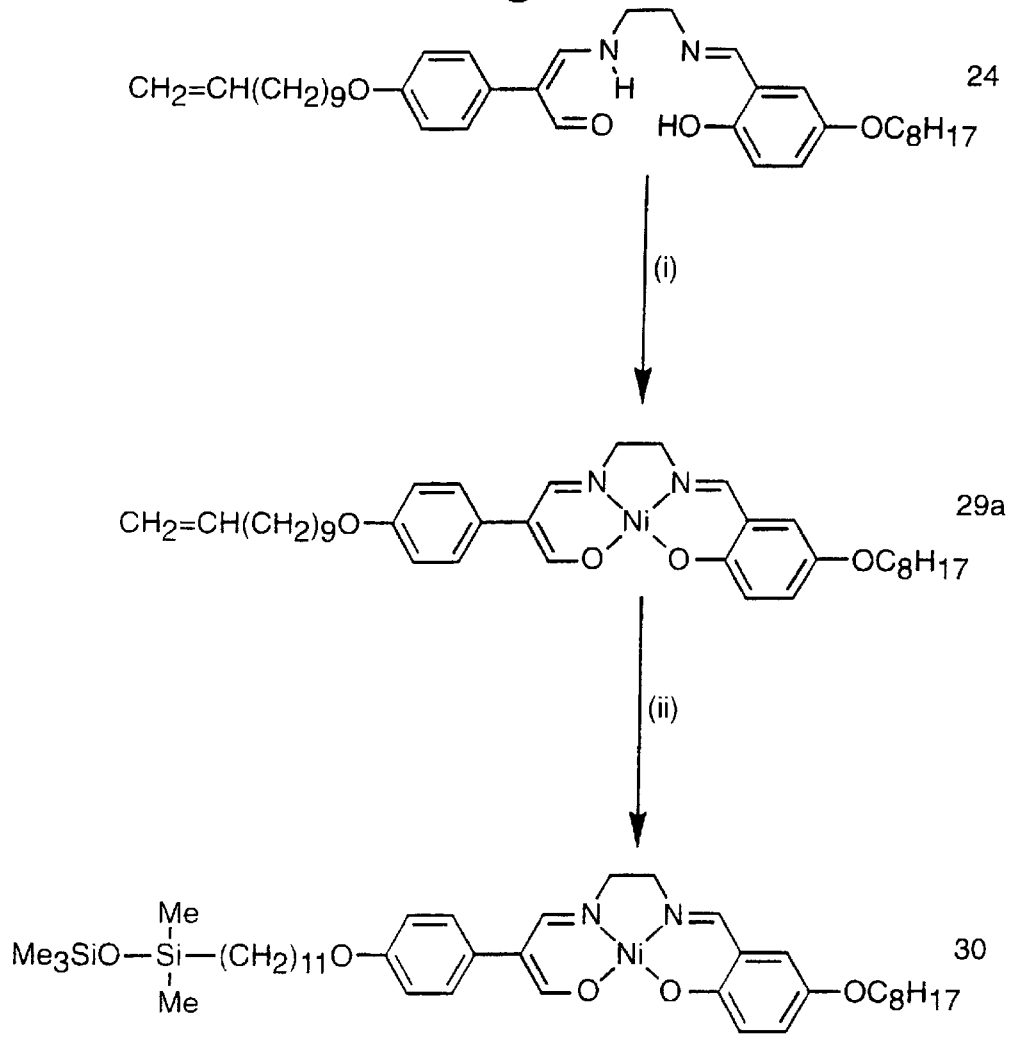
(i) [Ni(OAc)$_2$.4H$_2$O], C$_2$H$_5$OH, reflux, 1 h;
(ii) Me$_3$SiOSiMe$_2$H, toluene, [H$_2$PtCl$_6$], 7 days
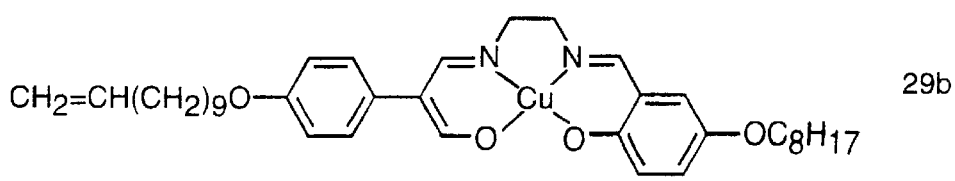

(i) 1,2-Diaminoethane / CH₂Cl₂

METAL-CONTAINING SIDE CHAIN LIQUID CRYSTAL POLYMERS

BACKGROUND OF THE INVENTION

This invention concerns Liquid Crystal materials including polymeric and non-polymeric materials, oligomers, intermediates and methods for their preparation. It has applicability in the areas of display technology, thin film magnetic materials for use in (for example) data storage, lubricants and anisotropically supported catalysts.

In liquid crystal polymers, the monomers can be attached together in essentially two ways. The liquid crystal part, or mesogenic unit, of the polymer may be part of the polymer backbone resulting in a main chain LC polymer. Alternatively, the mesogenic unit may be attached to the polymer backbone as a pendant group i.e. extending away from the polymer backbone. This results in a side chain LC polymer.

The side chain liquid crystal polymer can generally be thought of as containing a flexible polymer with rigid segments (the mesogenic unit) attached along its length by short units which may be flexible or rigid. It is the anisotropic, rigid section of the mesogenic units that display orientational order in the liquid crystal phases. In order to affect the phases exhibited by the liquid crystal and the subsequent optical properties there are many features which can be altered: some of these features are particularly pertinent to the side chain liquid crystal polymers e.g. the flexible part (known as the spacer group) that joins the mesogenic unit to the polymer backbone.

BRIEF DESCRIPTION OF THE DRAWINGS

FIG. 1 is a reaction scheme used to make compounds 5 and 6.

FIG. 3 is a reaction scheme used to make compounds 9–12.

FIG. 4 is a reaction scheme used to make compounds 13–15.

FIG. 9 is a reaction scheme used to make compounds 24–25,

FIG. 11 is a reaction scheme used to make compounds 29b and 30.

Figure 13:
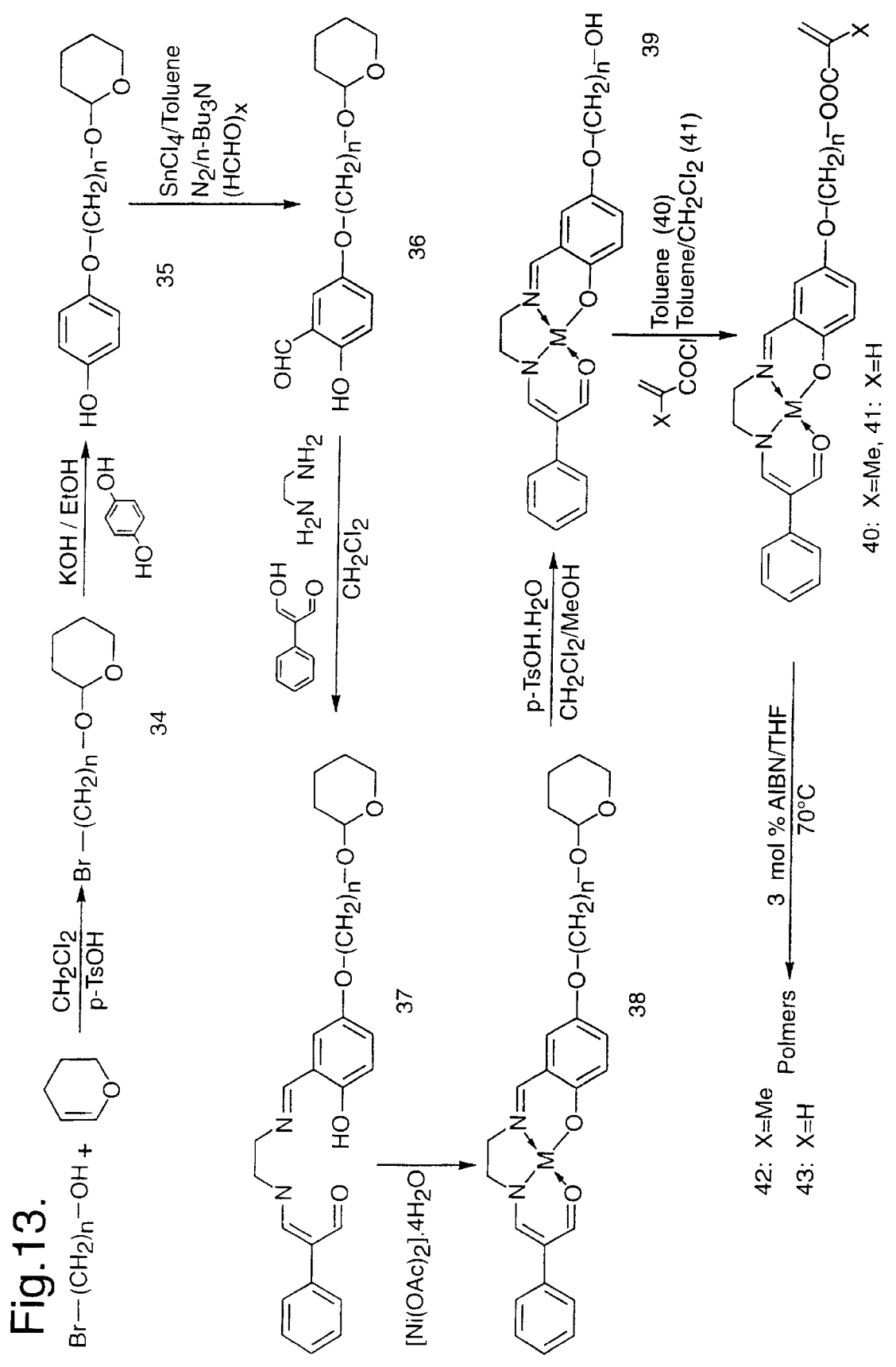

FIG. 13 is a reaction scheme used to make compounds 40–43.

DESCRIPTION OF THE INVENTION

Figure 2:
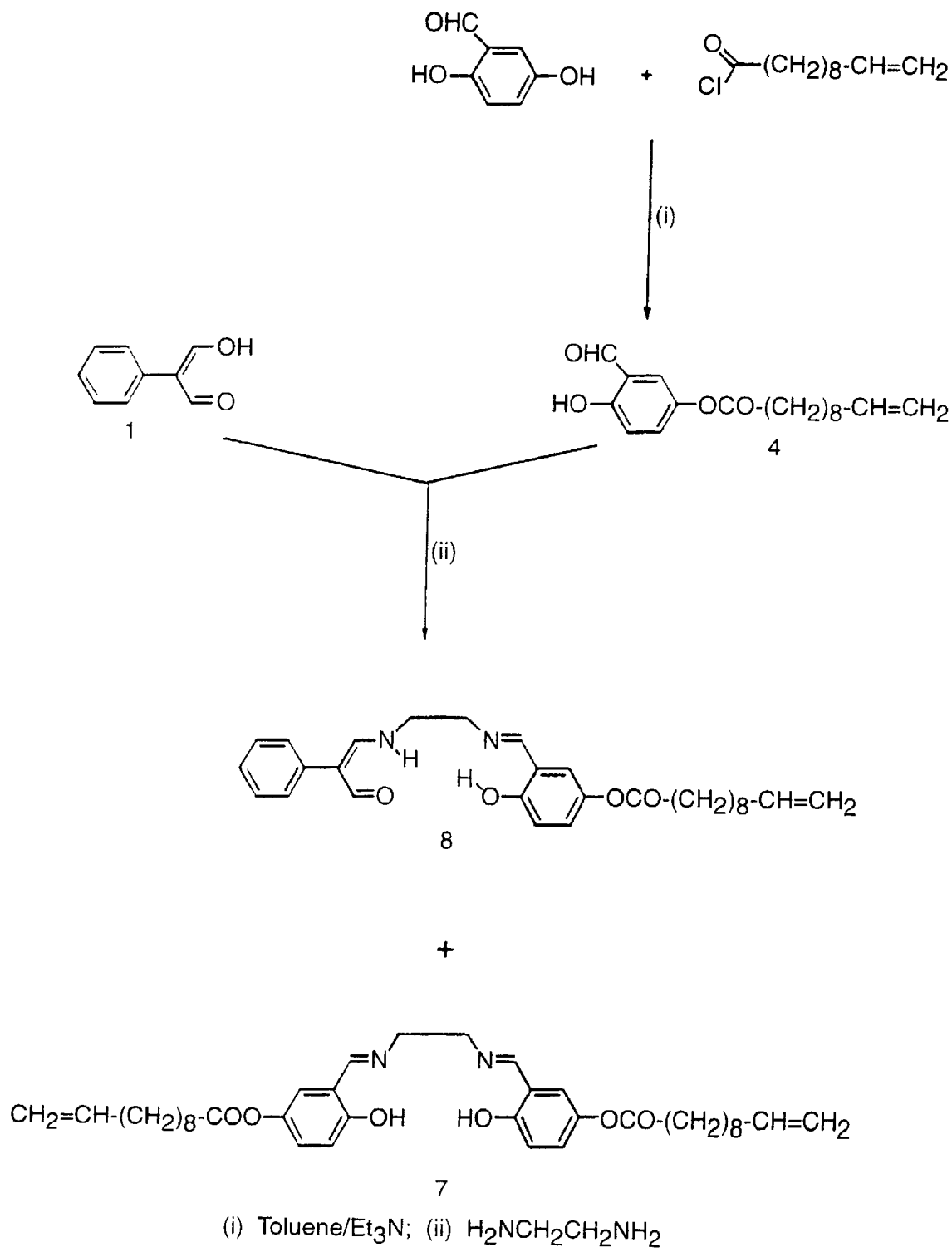
FIG. 2 is a reaction scheme used to make compounds 8 and 7.

According to a first aspect of this invention a set of compounds is defined by Formulas 1 and 2:

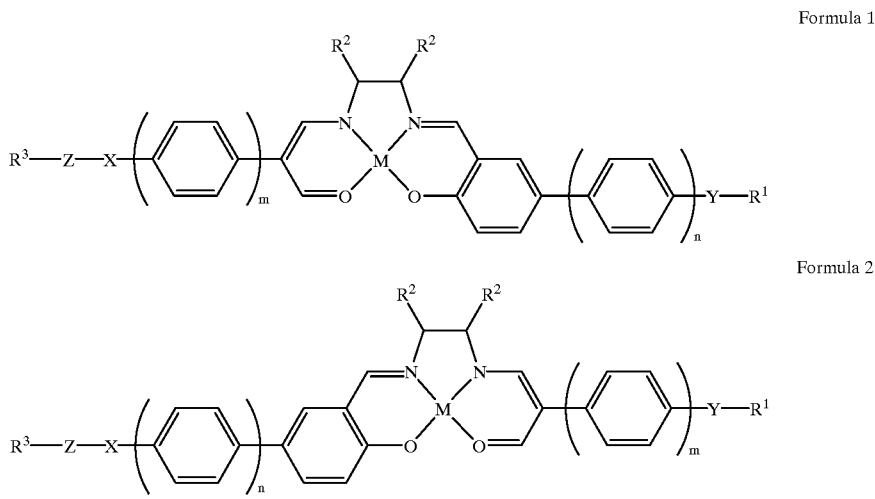

Formula 1

Formula 2 where:

$X =$ —OOC—, —COO—, —CO—, —O—, —S—, alkyne, σ-bond;

$Y =$ —OOC—, —COO—, —CO—, —O—, —S—, alkyne, σ-bond;

$Z =$ alkyl spacer;

$R^1 =$ alkyl ($C_kH_{2k+1}$);

$R^2 =$ H, F, $CH_3$;

$R^3 =$ alkyl, alkenyl, alkynyl, OH,

$CH_2=CH$—COO (acrylate), $CH_2=CH(CH_3)CHOO$ (methacrylate); and $m = 0, 1; n = 0, 1, 2;$ M is a transition metal.

Examples of these compounds include those defined by formulas 3 to 7 below.

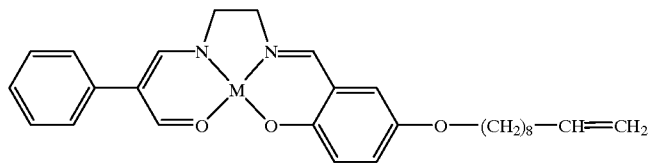

M = Ni or Cu

Formula 3

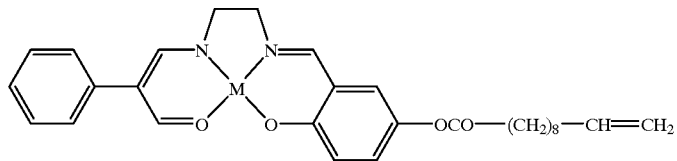

M = Ni, Cu or VO.

Formula 4

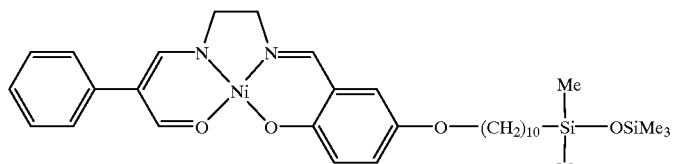

M = Ni or Cu.

Formula 5

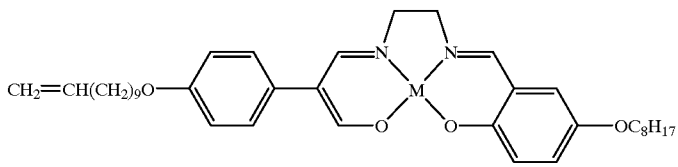

M = Ni or Cu.

formula 6

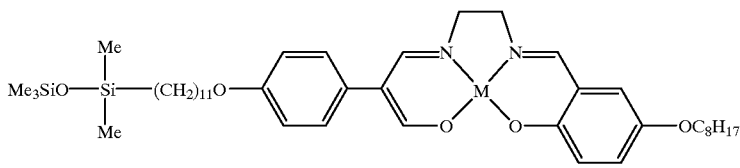

M = Ni or Cu formula 7

According to a second aspect of the invention, a method of synthesising oligomeric and polymeric liquid crystalline materials, substantially free from cross-linking, containing a co-ordinated transition metal centre in the mesogenic side chain, is characterised by the use of a non-symmetrical monomer, where only one moiety is activated towards polymerisation. Polymers which might be used with this second aspect of the invention include those defined by Formulas 8 and 9 below.

Formula 8

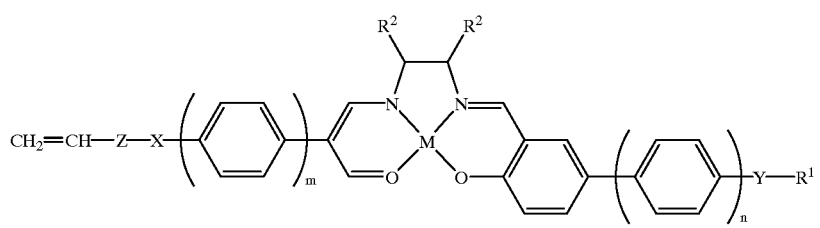

Formula 9

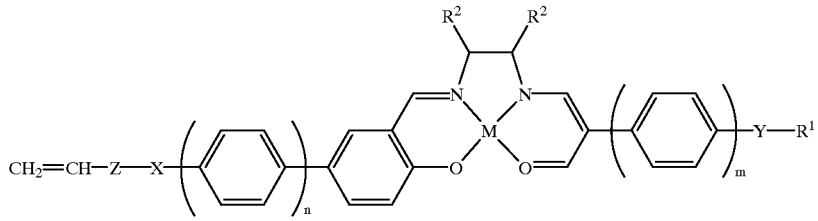

These include some compounds which are also in the set defined by Formulas 1 and 2 above, for example the compounds having Formulas 3, 4 and 6.

According to a third aspect of the invention, an oligomeric or polymeric liquid crystalline material, containing a co-ordinated transition metal centre in the mesogenic side chain, has a repeat unit represented by formula 10 or 11:

Formula 10

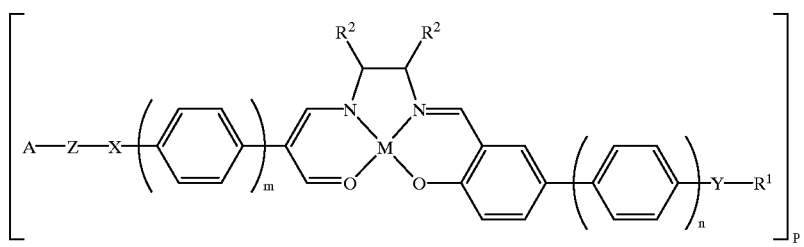

Formula 11

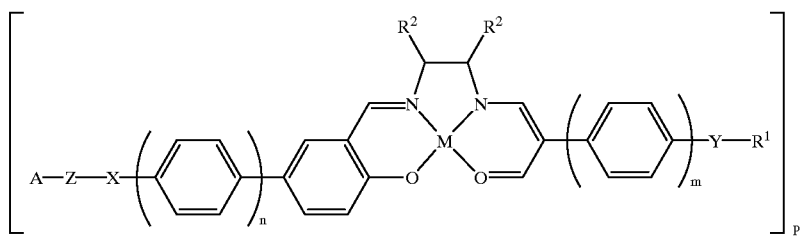

where:

X=—OOC—, —COO—, —CO—, —O—, —S—, alkyne, halogen, σ-bond;

Y=—OOC—, —COO—, —CO—, —O—, —S—, alkyne, halogen, σ-bond;

Z=alkyl, chiral alkyl, alkyne, halogen, poly(ether);

$R^1$=$C_kH_{2k+1}$, $C_kF_{2k+1}$, or intermediate degrees of fluorination, poly(ether), chiral functionality;

$R^2$=H, F, $CH_3$;

$R^3$=alkyl, alkenyl, alkynyl, OH,

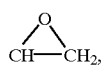

$CH_2$=CH—COO (acrylate), $CH_2$=CH($CH_3$)CHOO (methacrylate), m=0, 1; n=0, 1, 2;

M is a transition metal;

P represents the degree of polymerisation and

A is an oligomeric or polymeric modifier, for example:

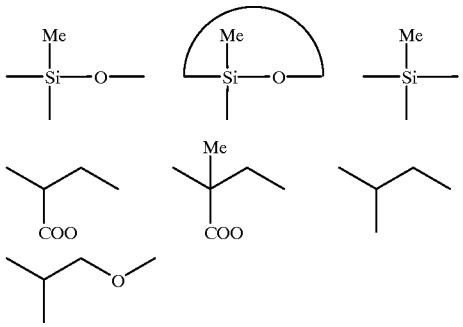

or $([SiO_{3/2}][SiR_2{}^4O]_b)_a$ wherein
  a=integer from 4 to 18;
  b=integer from 0 to 10 and
  $R^4$=alkyl group.

Examples of such polymers include those defined by Formulas 12 and 13 below.

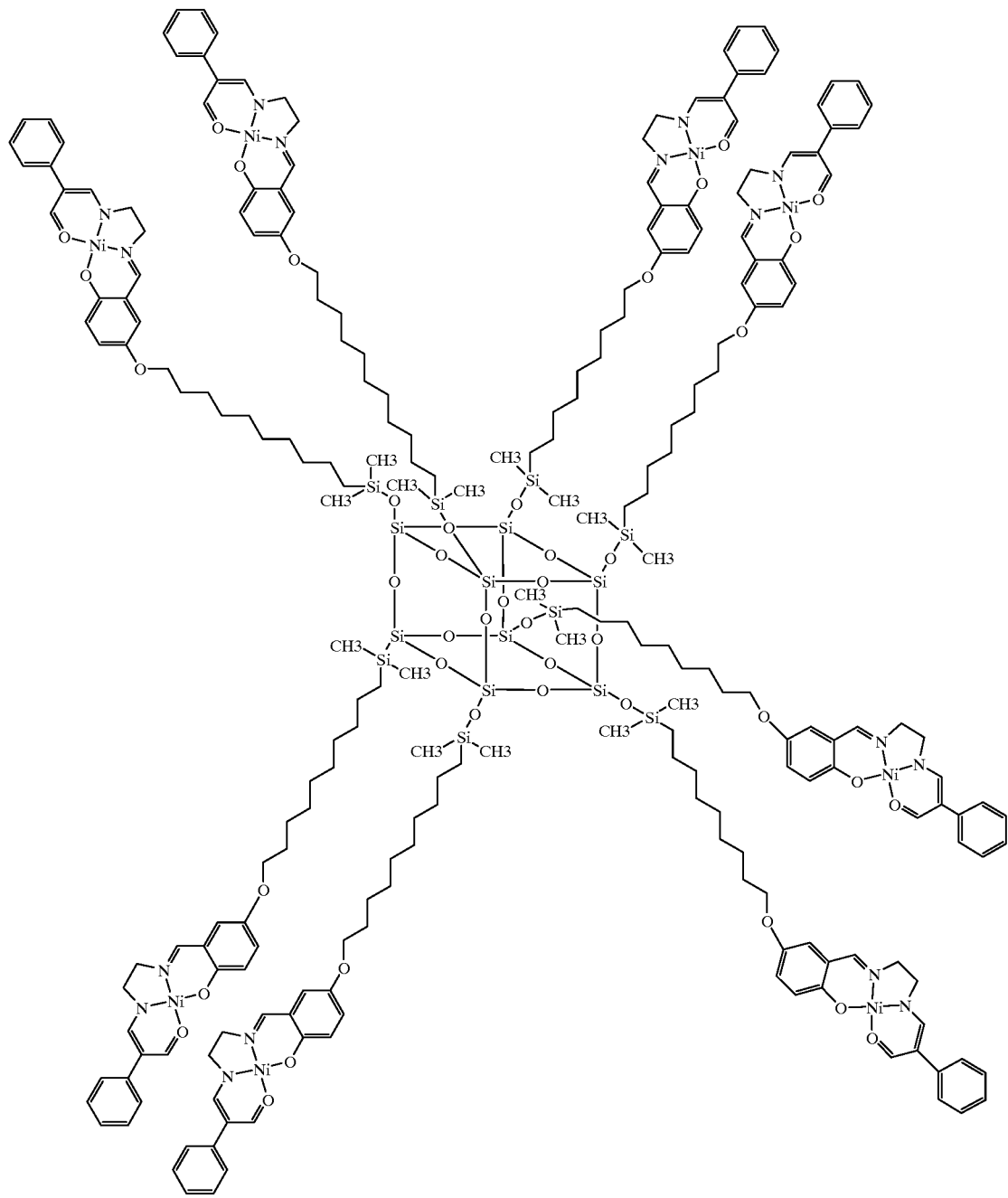
Formula 12

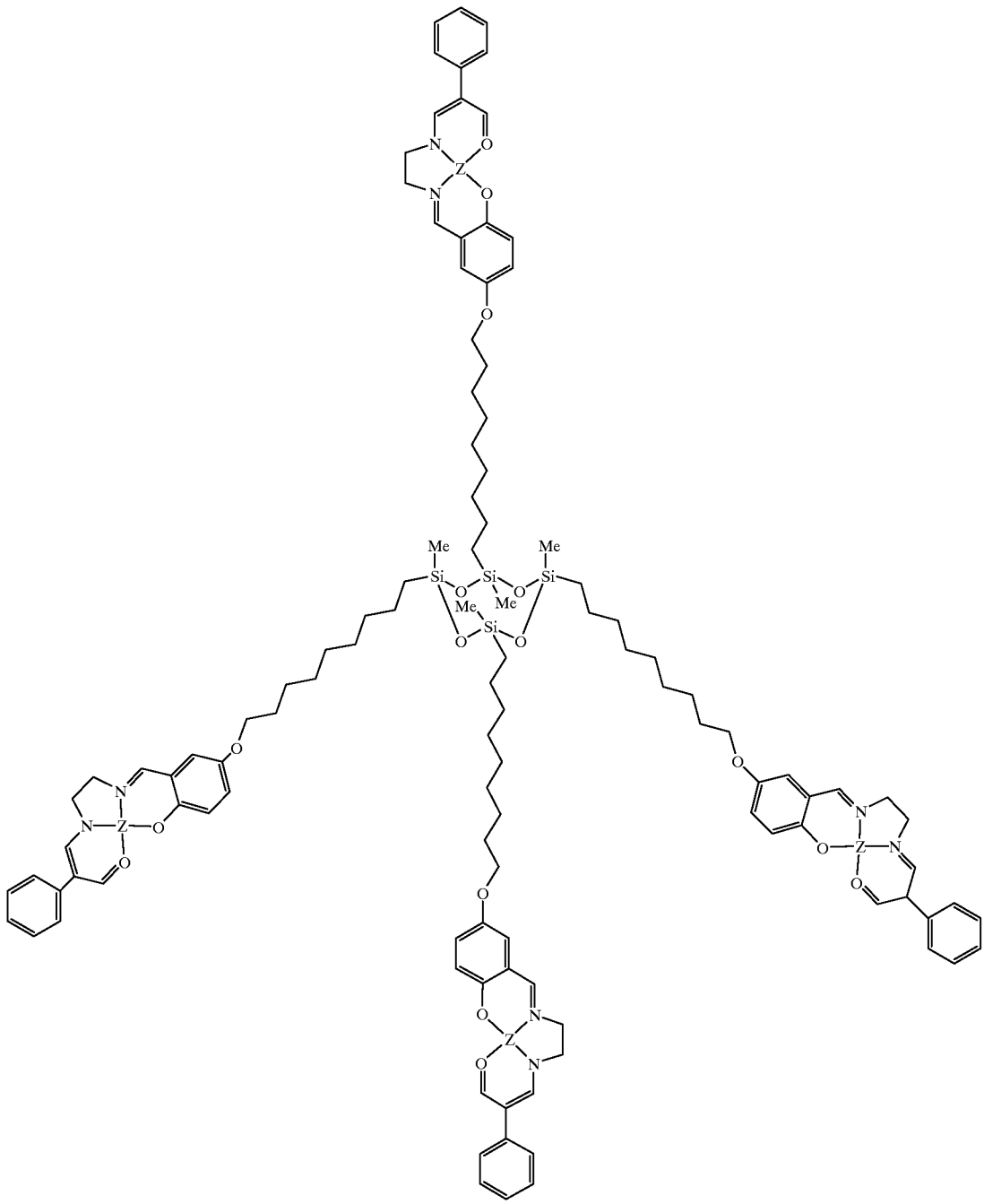
Formula 13
According to another aspect of the invention a poly(dimethylsiloxy) liquid crystalline material has a Formula 14:
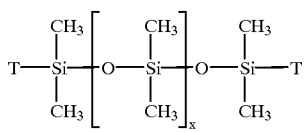
Formula 14
wherein x is an integer greater than, or equal to, 0 and T is a group having a general formula 15 or 16 below

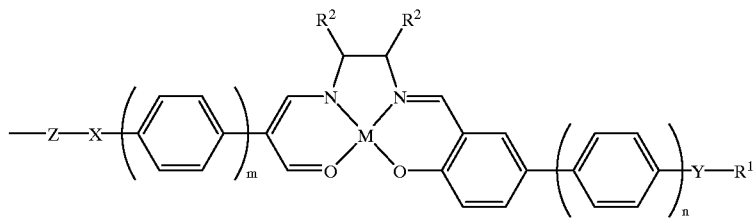

Formula 15

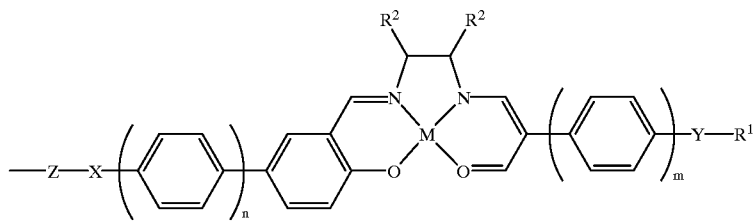

Formula 16 where:

X= —OOC—, —COO—, —CO—, —O—, —S—, alkyne, halogen, σ-bond;

Y= —OOC—, —COO—, —CO—, —O—, —S—, alkyne, halogen, σ-bond;

Z=alkyl, chiral alkyl, alkyne, halogen, poly(ether);

$R^1 = C_kH_{2k+1}$, $C_kF_{2k+1}$, or intermediate degrees of fluorination, poly(ether), chiral functionality;

$R^2$=H, F, $CH_3$; m=0, 1; n=0, 1, 2; M is a transition metal.

According to another aspect of the invention, a trimethylsiloxy-poly(dimethylsiloxy) liquid crystalline material has a general Formula 17

Formula 17

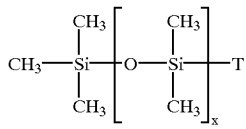

wherein x is an integer greater than, or equal to, 1 and T is a group having a general formula 15 or 16 above.

Figure 5:
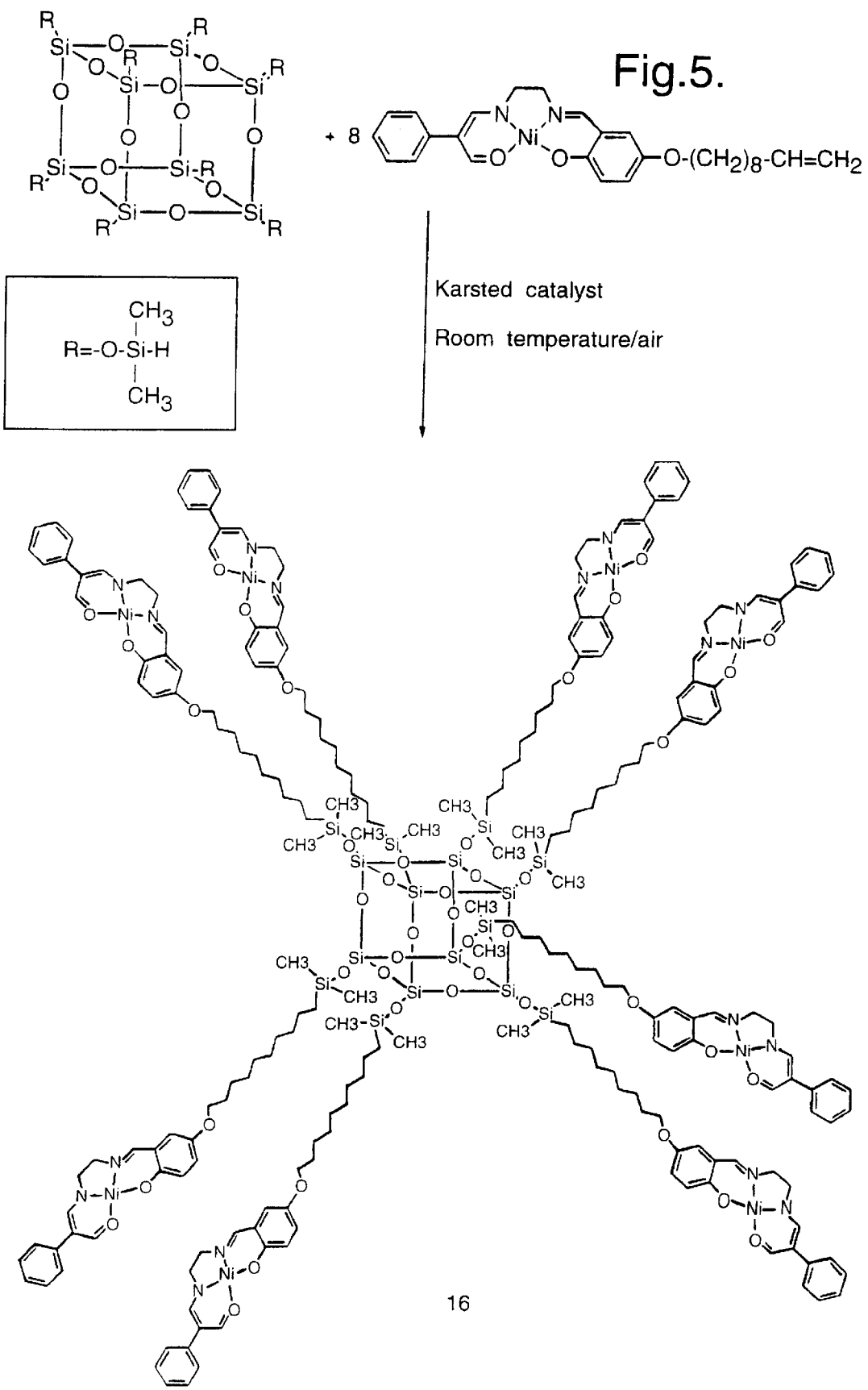
FIG. 5 is a reaction scheme used to make compounds 16.
Figure 6:
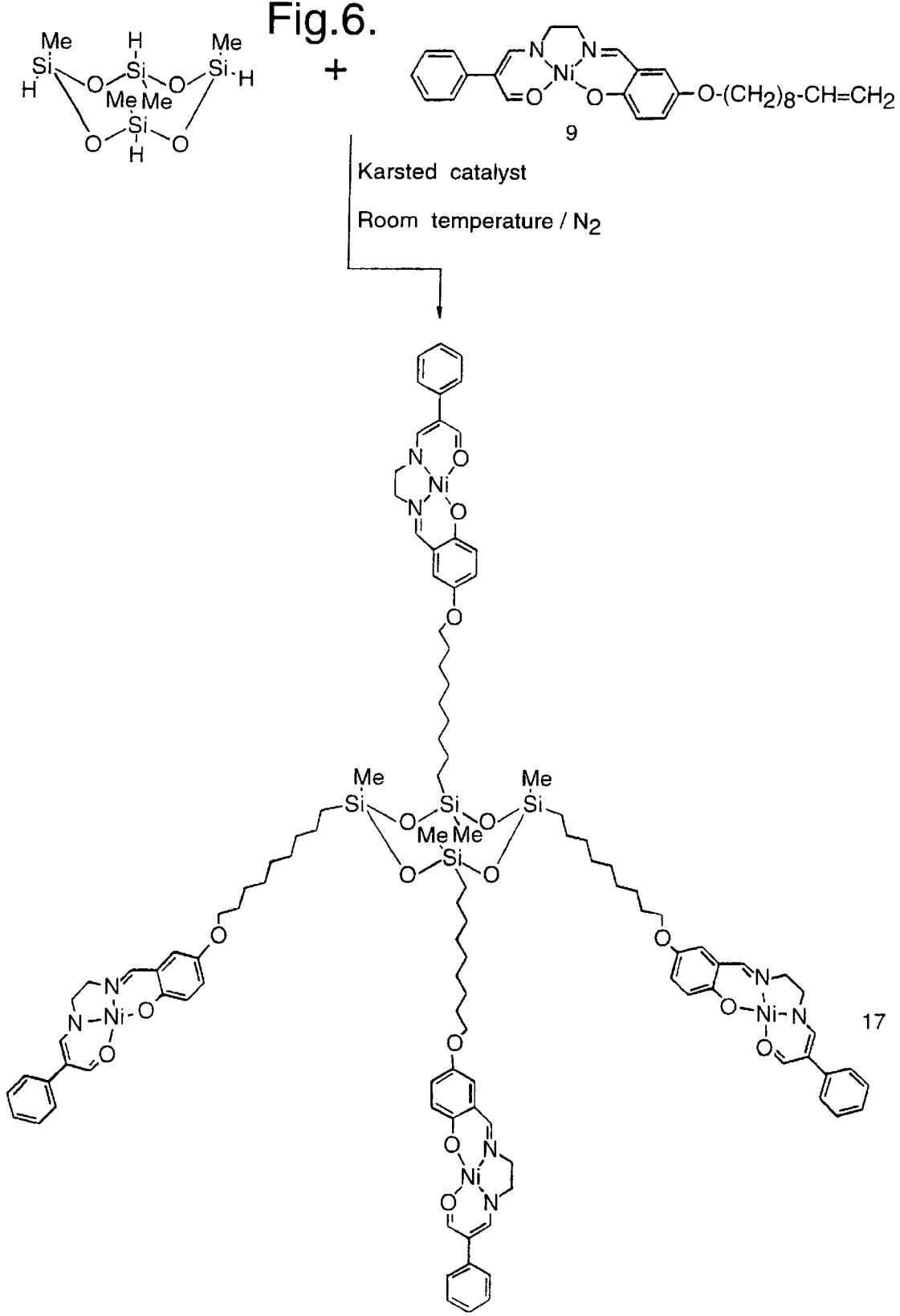
FIG. 6 is a reaction scheme used to make compounds 17.
Figure 7:
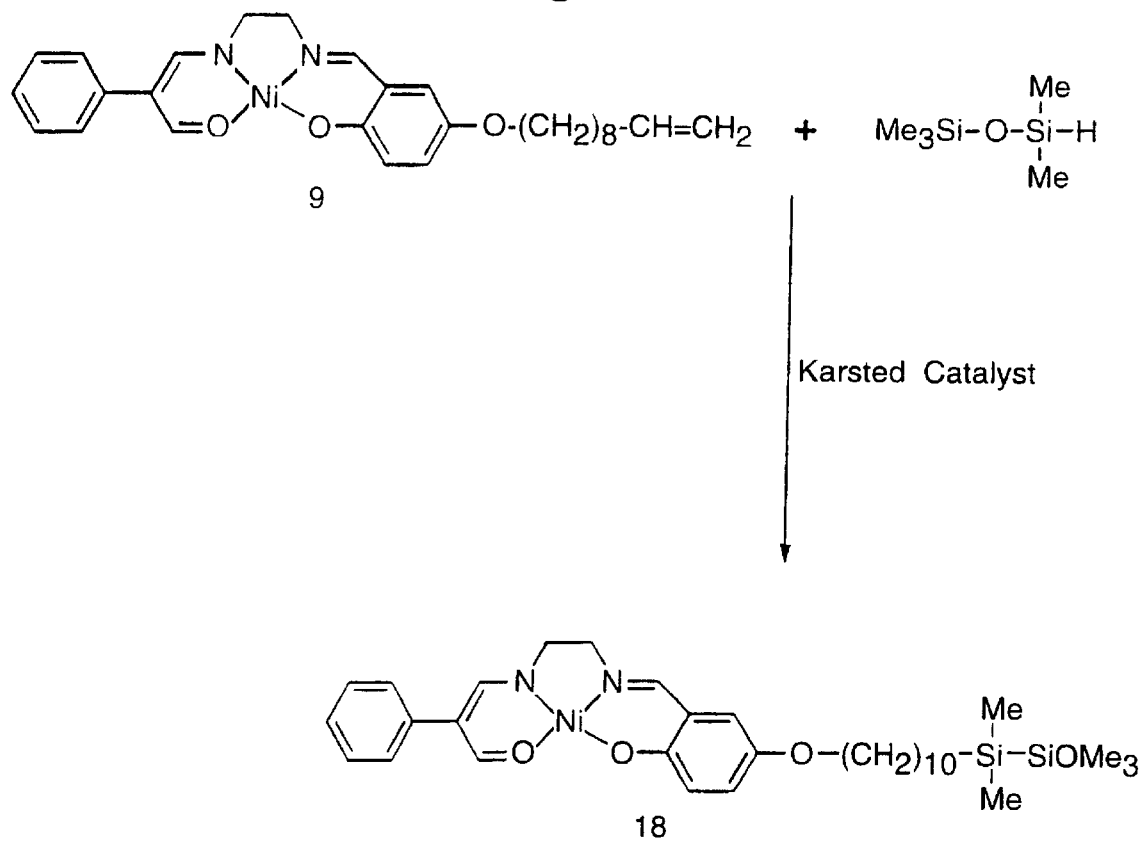
FIG. 7 is a reaction scheme used to make compounds 18.
Figure 8:
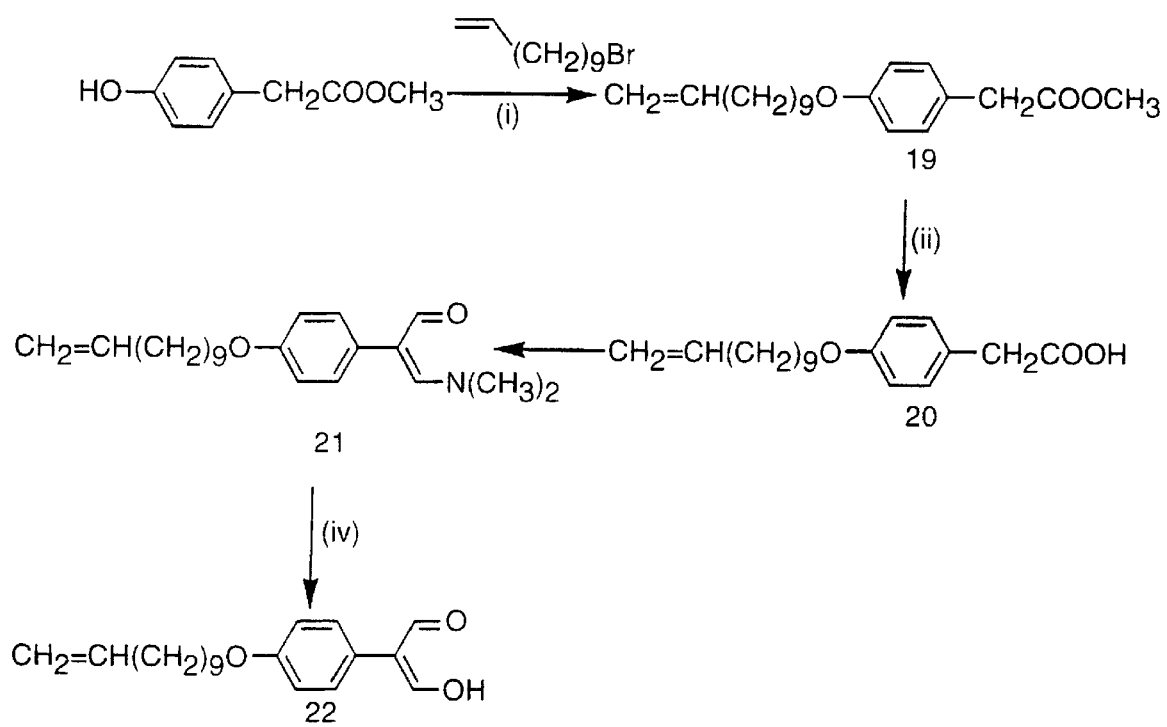
FIG. 8 is a reaction scheme used to make compounds 22.
Figure 10:
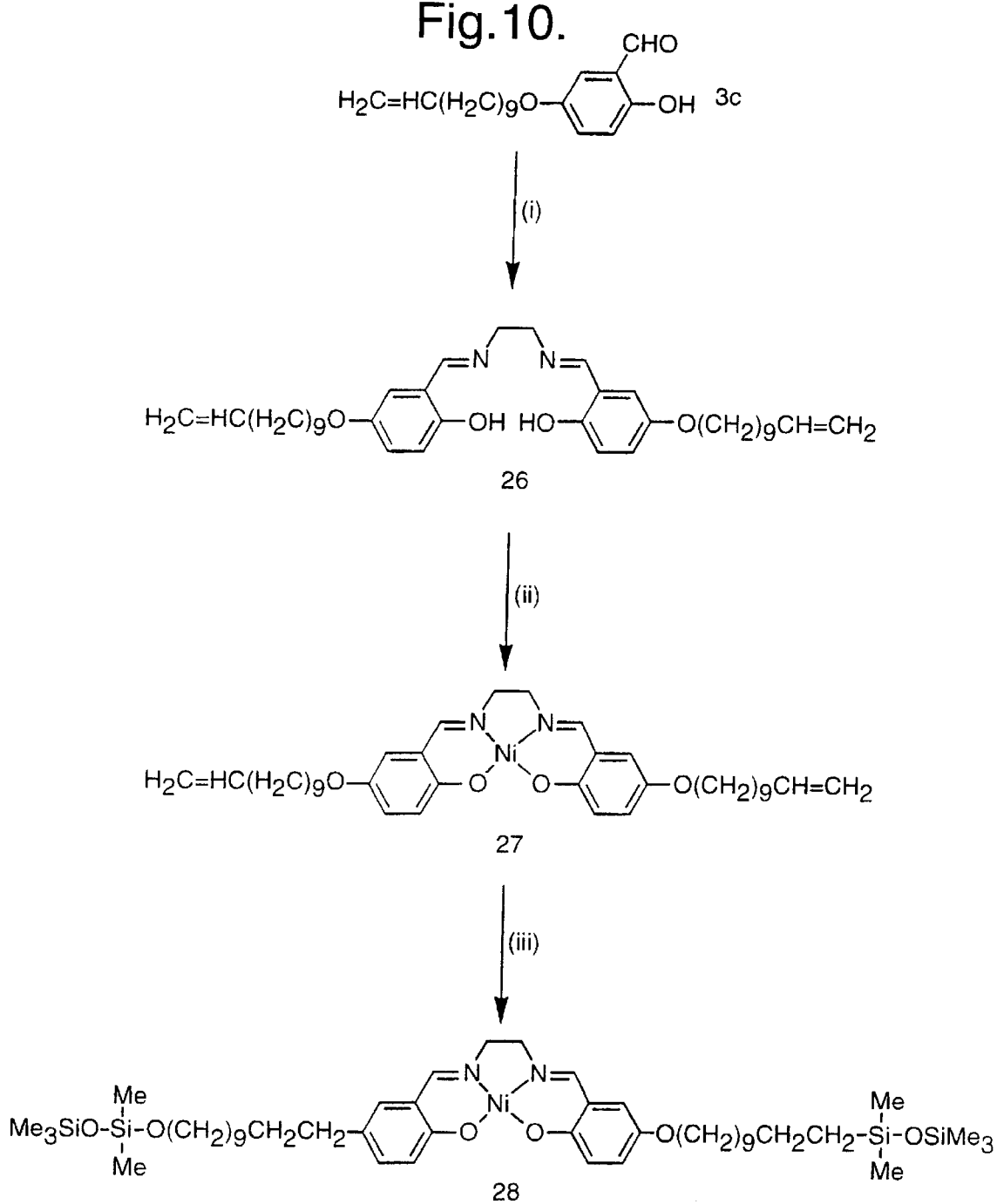
FIG. 10 is a reaction scheme used to make compounds 28.
Figure 12:
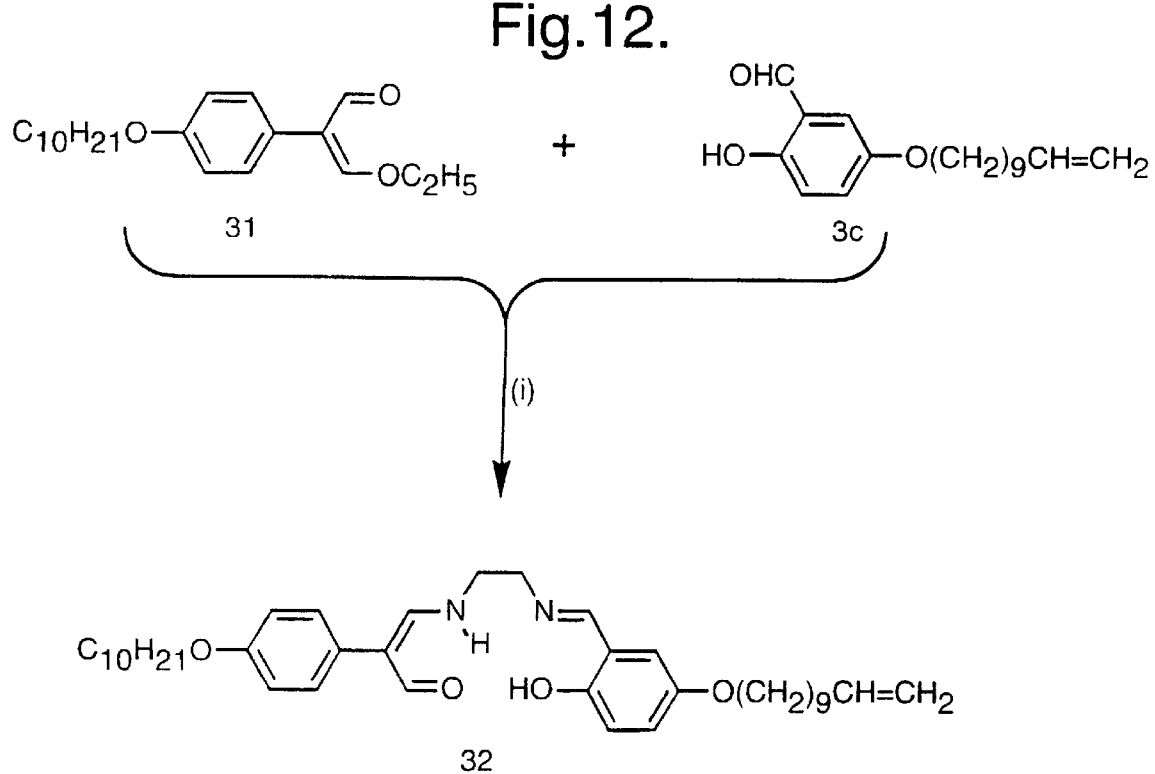
FIG. 12 is a reaction scheme used to make compounds 32.
Figure 14:
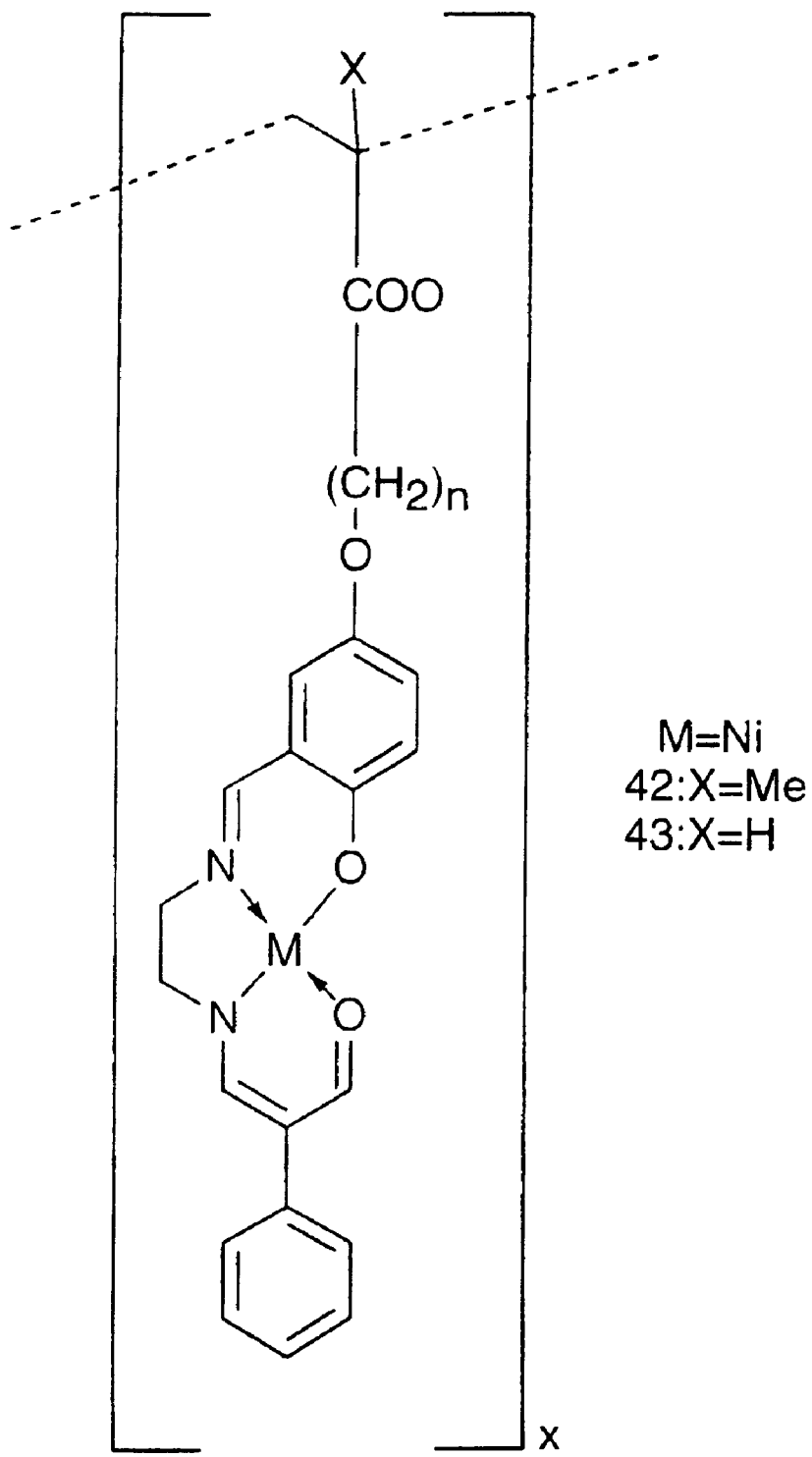
FIG. 14 is a reaction scheme used to make compounds 42–43.

The invention will now be described with reference to FIGS. 1 to 14 which show a selection of reaction schemes used to make materials of the current invention by methods of the current invention.

Experimental Procedures

1. Materials and Instrumentation

Solvents were dried over appropriate drying agents and distilled prior use. Metal acetate salts were purchased from Aldrich and used as received.

Infrared spectra were recorded on a Perkin-Elmer 783 spectrometer. NMR spectra were recorded on a Jeol JNM-GX spectrometer ($^1$H, 270 MHz; $^{13}$C, 67.80 MHz; $^{29}$Si, 53.54 MHz); chemical shifts are reported in parts per million (δ) with reference to internal $SiMe_4$ or residual protonated species of the deuterated solvent used for $^1$H and $^{13}$C analysis. $^{29}$Si NMR was externally referenced to $SiMe_4$; $Cr(acac)_3$ was added to aid the fast relaxation of the sample. Elemental analysis was performed on a Fisons Instruments Carlo Erba EA 1108 CHN analyser using acetanilide as the reference standard. $V_2O_5$ was added to aid combustion in a number of cases. Mass spectra were recorded on a Finnigan 1020 GC-MS spectrometer (electron ionisation mode/70 eV) and on a Kratos MS80 spectrometer (fast atom bombandment mode/NOBA matrix). Molecular weight determinations were carried out on a Knauer vapour osmometer.

Differential scanning calorimetry was performed on a Perkin-Elmer DSC2 calorimeter. Phase transitionn temperatures are given as the endothermic onset of the second heating cycle (scan rate 10° C. min$^{-1}$). The results were standardised with respect to indium (measured onset 156.60° C., ΔH=28.47 J g$^{-1}$; literature value 156.60° C., ΔH=28.45 J g$^{-1}$). Optical analysis was carried out on a Nikon POH polarising microscope equipped with a Metler FP82 microfurnace in conjunction with a FP80 Central Processor.

2. Synthetic Procedures (2-Phenyl)-3-hydroxyprop-2-enal, (1)

This was prepared according to literature procedures (A. Liepa; *Aust. J. Chem.*, 1981, 34, 2647).

4-Alkoxy and 4-(ω-alkenyloxy)phenols, (2)

These were prepared by standard alkylation of hydroquinone (Aldrich) with commercial n-alkyl bromides (Aldrich) or ω-alkenyl bromides (Lancaster) For example:

4-(Dec-9-enyloxy)phenol, (2).

Hydroquinone (37.65 g, 342 mmol) and dec-9-enyl bromide (25 g, 114 mmol) were dissolved in ethanol (150 ml) with warming under a nitrogen atmosphere. The solution was heated under reflux and a solution of potassium hydroxide (6.83 g, 121 mmol) in water (20 ml) was added dropwise over 1 h. The resulting suspension was heated under reflux (3 H) then poured on to water (500 ml) and extracted with ether (3×100 ml). The combined extracts were dried ($MgSO_4$), evaporated in vacuo and the residue extracted with heptane (300 ml). On cooling, it afforded a first crop of the phenol (10.31 g). The remaining material was chromatographed (flash grade silica gel, petroleum ether 40–60° C./diethyl ether 3/2). 2 was isolated as white plates ($R_f$= 0.57). Combined yield=15.61 g (55%). Mp=54° C.

$^1$H NMR (CDCl$_3$): δ 6.78 (m, 4H, aromatic); 5.81 (d($J_{trans}$=17 Hz) d($J_{cis}$=10 Hz)t($J_{fg}$=7 Hz), 1H, $CH_{2=CH}$);

4.99 (d($J_{trans}$=17 Hz) m. 1H, $H_e$); 4.93 (d($J_{cis}$=10 Hz) m. 1H, $H_d$); 4.63(s, 1H, OH); 3.89 (t(J=7 Hz), 2H, $CH_2O$); 2.04 (m, 2H. $CH_2$—CH=): 1.73 (m, 2H, $CH_2$—$CH_2$—O); 1.30 (m, 10H. $(CH_2)_5$).

2-Hydroxy-5-substituted-benzaldehydes were prepared from the corresponding 4-substituted phenols according to a method similar to the one used for the unsubstituted derivative (G. Casiraghi, G. Casnati, G. Puglia, G. Sartori, G. Terenghi; *J. Chem. Soc.* Perkin 1, 1980, 1862.). For example:

2-Hydroxy-5-(dec-9enyloxy)benzaldehyde, (3a)

$SnCl_4$ (0.27 ml, 2.33 mmol) was added to a solution of 4-(dec-9-enyloxy)phenol (5.80 g, 23.33 mmol) in sodium dried, degassed toluene (250 ml) under a nitrogen atmosphere. Tri-n-butylamine (2.22 ml, 9.34 mmol) was added at room temperature. The solution truned yellow and was stirred for 1 h before paraformaldehyde (BDH) (1.54 g, 51 mmol) was added and the yellow suspension heated to 105° C. (3 h). The brown solution was cooled, poured onto saturated aqueous NaCl (200 ml) and acidified to pH 2 with 10% HCl. The product was extracted with esther (3×100 ml) and the combined organic layers dried ($MgSO_4$) and evaporated. The residue was purified by column chromatography (flash grade silica gel; petroleum ether 40–60° C./diethyl ether. 3/2). The title compound 3 was isolated as a yellow oil ($R_f$=0.62). Yield=2.44 g (38%).

$^1$H NMR ($CDCl_3$): δ 10.91 (s, 1H, OH); 9.85 (s, 1H, CHO); 7.32 (d(J=3 Hz), 1H, $H_a$); 7.24 (m, 1H, $H_b$); 7.0 (d(J=9 Hz), 1H, $H_c$); 5.81 (d($J_{trans}$=17 Hz) d($J_{cis}$=10 Hz) t($J_{fg}$=7 Hz), 1H, $CH_2$=CH); 4.99 (d($J_{trans}$=17 Hz) m, 1H, $H_e$); 4.93 (d($J_{cis}$=10 Hz) m, 1H. $H_d$); 3.87 (t(J=7 Hz), 2H, $CH_2O$); 2.04 (m, 2H, $CH_2$—$CH_2$—O); 1.30 (m, 10H, $(CH_2)_5$).

2-Hydroxy-5-alkyl- (or alkenyl-) carbonyloxybenzaldehydes were prepared by standard esterification of 2,5-dihydroxy benzaldehyde with the corresponding commercially available alkanoyl (or ω-akenoyl) chlorides. For example:

2-Hydroxy-5-(dec-9-enylcarbonyloxy) benzaldehyde, (4)

Triethylamine (2.22 g, 14.48 mmol) was added to a solution of 2,5-deihydroxybenzaldehyde (Fluka) (2.0 g, 14.48 mmol) in sodium dried toluene (300 ml), followed by dropwise addition of 10-undecenoyl chloride (Aldrich) (4.40 g, 14.48 mmol) in toluene (30 ml) of over a period of 2 h. The suspension was stirred (18 h). filtered and the solution evaporated to dryness. 4 was obtained as thin white needles from methanol after column chromatograghy (flash grade silica gel; petroleum ether/ethyl acetate, 4/1). $R_f$=0.52. Yield=3.39 g (77%).

$^1$H NMR ($CDCl_3$): δ 10.91 (s, 1H, OH); 9.85 (s, 1H, CHO). 7.32 (d(J=3 Hz), 1H. $H_a$); 7.24 (m, 1H, $H_b$); 7.0 (d(J=9 Hz), 1H, $H_c$); 5.81 (d($J_{trans}$=17 Hz) d($J_{cis}$=10 Hz) t($J_{fg}$=7 Hz), 1H, $CH_2$=CH); 4.99 (d($J_{trans}$=17 Hz) m, 1H, $H_e$); 4.93 (d($J_{cis}$=10 Hz) m, 1H. $H_d$); 2.56 (t(J=7 Hz), 2H, $CH_2COO$); 2.04 (m, 2H, $CH_2$—CH=); 1.73 (m, 2H, $CH_2$—$CH_2$—O); 1.30 (m, 10H, $(CH_2)_5$).

The ligands were prepared by condensation of an appropriate 2-phenyl-3-hydroxypropenal, 1,2-diaminoethane and a 2-hydroxy-5-substituted benzaldehyde in equimolar amounts in $CH_2Cl_2$ solution, with continuous removal of water. This procedure afforded both the symmetrical salen ligand and the unsymmetrical ligand. For example:

8-(3-Dec-9-enyloxy-6-hydroxyphenyl)-2-phenyl-4,7-diazocta-2,7-dien-1-al (6)

1,2-Diaminoethane (0.2 g, 3.36 mmol) was added to a vigorously stirred solution of 2-phenyl-3-hydroxypropenal (0.498 g, 3.36 mmol) in $CH_2Cl_2$ (300 ml). A white precipitate formed immediately. 2-Hydroxy-5-(dec-9-enyloxy) benzaldehyde (0.93 g, 3.36 mmol) was added and the yellow suspension was stirred at room temperature (18 h) and then heated under reflux (5 h) using a Dean-Stark apparatus protected from moisture with a calcium chloride guard tube. The yellow solution was evaporated in vacuo and the residue purified by column chromatography (flash grade silica gel; $CH_2Cl_2$/THF, 4/1). The band with $R_f$=0.76 yielded 1,6-di(3-dec-9-enyloxy-6-hydroxyphenyl)-2,5-diazahexa-1,5-diene (5) after recrystallisation from ethanol (yield=0.19 g, 40%). The band with $R_f$0.50 was collected and the product recrystallised from ethanol to yield bright yellow crystals of 6. Yield=0.46 g (61%).

Spectral and Analytical Data for 5

Microanalysis: Calculated for $C_{36}H_{52}O_4N_2$: C, 74.96; H. 9.07; N, 4.85. Found: C, 74.81; H, 9.19; N, 4.81.

$^1$H NMR ($CDCl_3$): δ 12.69 (s, 1H, OH); 8.30 (s, 1H, CHO). 6.96–6.70 (m. 3H. aromatic); 5.81 (d($J_{trans}$=17 Hz) d($J_{cis}$=10 Hz) t($J_{fg}$=7 Hz), 1H. $CH_2$=CH); 4.99 (d($J_{trans}$=17 Hz) m, 1H, $H_e$); 4.93 (d($J_{cis}$=10 Hz) m, 1H, $H_d$); 3.93 (s, 2H. N=$CH_2$): 3.87 (t(J=7 Hz), 2H. $CH_2O$); 2.04 (m, 2H, $CH_2$—CH=); 1.73 (m, 2H, $CH_2$—$CH_2$—O); 1.30 (m, 10H. $(CH_2)_5$).

Spectral and Analytical Data for 6

Microanalysis: Calculated for $C_{28}H_{34}O_3N_2$: C, 74.97; H. 8.08; N. 6.24. Found: C, 74.66; H. 8.12; N, 6.21.

MS (EI): m/z 448 ($M^{+)}$; 420 ($M^+$—CO). Mp=136° C.

$^1$H NMR ($CDCl_3$): δ 12.45 (s, 1H, OH); 10.48 (m broad. 1H. NH); 9.47 (d(J=4 Hz), 1H, CHO); 8.31 (s, 1H, CH=N); 7.30–6.72 (m, 9H. aromatic $C_6H_5$, $H_a$, $H_b$, $H_c$, NCH=C); 5.81 (d($J_{trans}$=17 Hz) d($J_{cis}$=10 Hz)t($J_{fg}$=7 Hz), 1H, $CH_2$=CH); 4.99 (d($J_{trans}$=17 Hz) m, 1H, $H_e$); 4.93 (d($J_{cis}$=10 Hz) m, 1H, $H_d$); 3.88 (t(J=7 Hz), 2H, $CH_2O$); 3.81 (m, 2H. $CH_2$—N=CH); 3.65 (m, 2H, $CH_2$—NH); 2.04 (m, 2H, $CH_2$—CH=); 1.70 (m, 2H, $CH_2$—$CH_2$—O); 1.30 (m, 10H, $(CH_2)_5$).

8-(3-Dec-9-enylcarbonyloxy-6-hydroxyphenyl)-2-phenyl-4,7-diazocta-2,7-dien-1-al, (8)

1,2-Diaminoethane (0.33 ml. 5.0 mmol) was added dropwise to a solution of 2-phenyl-3-hydroxypropenal (0.740 g, 5.0 mmol) in $CH_2Cl_2$ (500 ml). A white precipitate formed immediately, 2-Hydroxy-5-(carbonyldec-9-enyloxy) benzaldehyde (4) (1.52 g, 5.0 mmol) was added and the suspension was stirred vigorously at room temperature (18 h) and then heated under reflux using a Dean-Stark apparatus protected from moisture (5 h) to give a yellow clear solution. The solvent was removed in vacuo and the yellow crude product purified by column chromatography (flash grade silica gel; $CH_2Cl_2$/THF. 22/3). The first yellow band ($R_f$=0.76) afforded 1,6-di(3-dec-9-enylcarbonyloxy-6-hydroxyphenyl)-2,5-diazahexa-1,5-diene (7) after recrystallisation from ethanol (yield=0.33 g. 41%). The second yellow band ($R_f$=0.55) was collected and recrystallised from ethanol to give 8 as yellow crystals. Yield=0.56 g (47%).

Spectral and Analytical Data for 7

Microanalysis: Calcd for $C_{38}H_{52}O_6N_2$: C, 72.12: H, 8.27: N, 4.42. Found: C, 72.40; H, 8.47; N, 4.40.

MS (EI): m/z 632 ($M^+$), 466 ($M^+$-$COC_{10}H_{21}$), 301 ($M^+$—2x($COC_{10}H_{21}$)).

$^1$H NMR ($CDCl_3$): δ 13.05 (s, 1H, OH); 8.31 (s, 1H, HC=N); 7.04–6.89 (m, 3H. aromatic); 5.81 (d($J_{trans}$=17

Hz) d($J_{cis}$=10 Hz)t($J_{fg}$=7 Hz), 1H. CH$_2$=CH); 4.99 (d($J_{trans}$=17 Hz) m. 1H, H$_e$); 4.93 (d($J_{cis}$=10 Hz) m, 1H, H$_d$); 3.93 (s, 2H, N=CH$_2$); 2.52 (t(J=7 Hz), 2H. CH$_2$COO); 2.04 (m, 2H, CH$_2$—CH=); 1.73 (m, 2H, CH$_2$—CH$_2$—O); 1.30 (m, 10H, (CH$_2$)$_5$).

Spectral and Analytical Data for 8

Microanalysis: Calcd for C$_{29}$H$_{36}$O$_4$N$_2$: C, 73.08; H, 7.60: N, 8.87. Found: C, 72.74; H, 7.72; N, 5.85.

MS (EI): m/z 476 (M$^+$), 311 (M$^+$—COC$_{10}$H$_{18}$).

$^1$H NMR (CDCl$_3$): δ 12.85 (s, 1H, OH); 10.49 (m broad, 1H. NH); 9.48 (d(J=4 Hz), 1H, CHO); 8.32 (s, 1H, CH=N); 7.33–6.92 (m, 9H. aromatic C$_6$H$_5$, H$_a$,H$_b$, H$_c$, NCH=C); 5.81 (d($J_{trans}$=17 Hz) d($J_{cis}$=10 Hz)t($J_{fg}$=7 Hz), 1H, CH$_2$=CH); 4.99 (d($J_{trans}$=17 Hz) m, 1H, H$_e$); 4.93 (d($J_{cis}$=10 Hz) m, 1H, H$_d$); 3.82 (m, 2H, CH$_2$—N=CH): 3.64 (m, 2H, CH$_2$—NH); 2.54 (t(J=7 Hz), CH$_2$—COO); 2.04 (m, 2H, CH$_2$—CH=); 1.73 (m, 2H, CH$_2$—CH$_2$COO); 1.30 (m, 10H, (CH$_2$)$_5$).

[8-(3-Dec-9-enyloxy-6-hydroxyphenyl)-2-phenyl-4,7-diazocta-1,3,7-trienato](2-) nickel(II), (9)

A suspension of nickel acetate tetrahydrate (0.1941 g, 0.78 mmol) in methanol (5 ml) was added to a solution of 6 (0.350 g, 0.78 mmol) in methanol (30 ml) which was heated to reflux. The red solution obtained was heated under reflux (1 h) and on cooling to room temperature produced red-brown needles that were filtered off, dried and recrystallised from methanol. Yield=0.355 g (90%). Mesomorphism: K 181 S$_A$ 190 Iso ° C.

Microanalysis: Calcd for C$_{28}$H$_{34}$O$_3$N$_2$Ni: C, 66.56; H, 6.77; N, 5.54. Found: C, 66.47; H, 6.65; N, 5.46.

MS (EI): m/z 504 (M$^+$-1); 365 (M$^+$-C$_{10}$H$_{19}$).

Molecular weight determination (CHCl$_3$); Calcd for C$_{28}$H$_{34}$O$_3$N$_2$Ni: 505.24; Found: 567.

IR (KBr disc,υ cm$^{-1}$): 1609 (vs, sharp; C=N, C=O and C=C—N coordinated).

$^1$H N MR (CDCl$_3$): δ 7.4-7.0 (m, 8H; aromatic C$_6$H$_5$, HC=N, HC=O and NCH=C): 6.91 (m, 2H, H$_a$,H$_b$); 6.48 (m, 1H, H$_c$); 5.81 (d($J_{trans}$=17 Hz)d($J_{cis}$=10 Hz)t($J_{fg}$=7 Hz), 1H, CH$_2$=CH); 4.99 (d($J_{trans}$=17 Hz)m, 1H, H$_e$); 4.93 (d($J_{cis}$=10 Hz)m, 1H,H$_d$); 3.79 (t(J=7 Hz), 2H, CH$_2$O); 3.34 (m, 4H, NCH$_2$); 2.04 (m, 2H, CH$_2$—CH=); 1.70 (m, 2H, CH$_2$—CH$_2$—O); 1.30 (m, 10H, (CH$_2$)$_5$).

[8-(3-Dec-9-enyloxy-6-hydroxyphenyl)-2-phenyl-4,7-diazocta-1,3,7-trienato](2-) copper(II), (10)

A solution of copper(II) acetate monohydrate (89 mg, 0.445 mmol) in methanol (5 ml) was added to a solution of 6 (0.20 g, 0.445 mmol) in methanol (10 ml) which was heated to reflux. The violet-green solution obtained was heated under reflux (1 h) and the green-brown solid formed on cooling to room temperature was filtered off and recrystallised from CH$_2$Cl$_2$/MeOH to afford 10 as a mass of violet-brown needles. Yield=0.16 g (68%). Mesomorphism: K (168 S$_A$) 186 Iso (° C.).

Microanalysis: Calcd for C$_{28}$H$_{34}$O$_3$N$_2$Cu: C, 65.93; H, 6.71; N, 5.48. Found: C, 65.63; H, 6.65; N, 5.41.

MS (EI): m/z 509 (M$^+$-1); 448 (M$^+$-Cu); 370 (M$^+$-C$_{10}$H$_{19}$).

Molecular weight determination (CHCl$_3$); Calcd for C$_{28}$H$_{34}$O$_3$N$_2$Cu: 510.0; Found: 510.9.

[1,6-Di(3-dec-9-enyloxy-6-hydroxyphenyl)-2,5-diazahexa-1,5-dienato](2-) nickel(II), (11)

Nickel(II) acetate tetrahydrate (0.1096 g, 0.44 mmol) was added to a refluxing solution of 5 (0.2540 g, 0.44 mmol) in absolute ethanol (20 ml). The resulting red solution was heated under reflux (1 h) and on cooling to room temperature afforded red needles that were filtered off and recrystallised from CH$_2$Cl$_2$/MeOH, to yield the title compound 11. Yield= 0.1967 g (75%). Mesomorphism: K 163 S$_A$ 261 Iso (° C.).

Microanalysis: Calcd for C$_{36}$H$_{50}$O$_4$N$_2$Ni: C, 68.27; H, 7.94; N, 4.42. Found: C, 68.12; H, 8.30; N, 4.41.

MS (EI): m/z 632 (M$^+$-1); 493 (M$^+$-C$_{10}$H$_{19}$); 355 (M$^+$-2×C$_{10}$H$_{19}$).

$^1$H NMR (CDCl$_3$); δ 7.21 (s. 2H, HC=N); 6.62–6.82 (m, 4H, H$_a$,H$_b$);; 6.34 (m, 2H, H$_c$); 5.81 (d($J_{trans}$=17 Hz)d($J_{cis}$=10 Hz)t($J_{fg}$=7 Hz), 2H, CH$_2$=CH); 4.99 (d($J_{trans}$=17 Hz)m, 2H, H$_e$); 4.93 (d($J_{cis}$=10 Hz)m, 2H,H$_d$); 3.78 (t(J=7 Hz), 4H, CH$_2$O); 3.40 (s, 4H, NCH$_2$); 2.02 (m, 4H, CH$_2$—CH=); 1.69 (m, 2H, CH$_2$—CH$_2$—O); 1.29 (m, 20H, (CH$_2$)$_5$).

[1,6-Di(3-dec-9-enyloxy-6-hydroxyphenyl)-2,5-diazahexa-1,5-dienato](2-) copper(II), (12)

Using the same procedure described above, 12 was obtained as violet-brown needles from CH$_2$Cl$_2$MeOH. Yield=93%. Mesomorphism: K 226 S$_A$ 239 Iso (dec) (° C.).

Microanalysis: Calcd for C$_{36}$H$_{50}$ O$_4$N$_2$Cu: C, 67.74; H, 7.88; N, 4.38. Found: C, 67.52; H, 7.80; N, 4.30.

MS (EI): m/z 639 (M$^+$+1), 576 (M$^+$-Cu).

[8-(3-Dec-9-enylcarbonyloxy-6-hydroxyphenyl)-2-phenyl-4,7-diazocta-1,3,7-trienato](2-) nickel(II), (13)

A solution of nickel(II) acetate tetrahydrate (0.1872 g; 0.734 mmol) in methanol (10 ml) was added to a refluxing solution of 8 (0.35 g, 0.734 mmol) in methanol (50 ml). The red solution was heated under reflux (1 h) and stored at –20° C. (18 h) to afford red crystals. The complex was recrystallised from methanol to afford 13 as red plates. Yield=0.32 g (81%). Mesomorphism: K 130 S$_A$ 211 Iso (° C.).

Microanalysis: Calcd for C$_{29}$H$_{34}$O$_4$N$_2$Ni: C, 65.32; H, 6.42; N, 5.25. Found: C, 65.19; H, 6.37; N, 5.14.

MS (EI): m/z 533 (M$^+$), 532 M$^+$-1), 366 (M$^+$-COC$_{10}$H$_{19}$, base peak).

IR (KBr disc; υ cm$^{-1}$): 1744 (vs, CO ester); 1609 (vs, sharp; C=N, C=O and C=C—N coordinated).

$^1$H NMR (CDCl$_3$): δ 7.42-6.82 (m, 11H, aromatic C$_6$H$_5$, H$_a$,H$_b$,H$_c$, NCH=CH, CHO, CH=N); 5.81 (d($J_{trans}$=17 Hz) d($J_{cis}$=10 Hz)t($J_{fg}$=7 Hz), 1H, CH$_2$=CH); 4.99 (d($J_{trans}$=17 Hz)m, 1H, H$_e$); 4.93 (d($J_{cis}$=10 Hz)m, 1H, H$_d$); 3.34 (m, 4H, N—(CH$_2$)$_2$—N); 2.50 (t(J32 7 Hz), CH$_2$—COO); 2.04 (m, 2H, CH$_2$—CH=); 1.73 (m, 2H, CH$_2$—CH$_2$COO); 1.30 (m, 10H, (CH$_2$)$_5$).

[8-(3-Dec-9-enylcarbonyloxy-6-hydroxyphenyl)-2-phenyl-4,7-diazocta-1,3,7-trienato](2-) copper(II), (14)

A solution of copper(II) acetate monohydrate (42 mg, 0.21 mmol) in methanol (3 ml) was added to a refluxing solution of 8 (0.100 g, 0.21 mmol) in methanol (15 ml). The resulting violet coloured solution was heated under reflux (1 h) and stored at 0° C. (18 h). The violet crystals formed were filtered off and recrystallized from CH$_2$Cl$_2$/MeOH to afford 14, as violet-green plates. Yield=80.1 mg (71%). Mesomorphism: K 143 S$_A$ 187 Iso (° C.).

Microanalysis: Calcd for C$_{29}$H$_{34}$O$_4$N$_2$Cu: C, 64.73; H, 6.36; N, 5.20. Found: C, 65.05; H, 6.54; N, 5.19.

MS (EI): m/z 538 (M$^+$), 476 (M$^+$-Cu).

IR (KBr disc; υ cm$^{-1}$): 1744 (vs, CO ester); 1609 (vs, sharp; C=N, C=O and C=C—N coordinated).

[8-(3-Dec-9-enylcarbonyloxy-6-hydroxyphenyl)-2-phenyl-4,7-diazocta-1,3,7-trienato](2-)oxovanadium(IV), (15)

A solution of oxovanadium(IV) sulphate pentahydrate (53 mg, 0.21 mmol) in a mixture of ethanol (2 ml) and water (1 ml) was added to a refluxing solution of 8 (0.100 g, 0.21 mmol) in ethanol (10 ml). Sodium acetate (68 mg, 0.82 mmol) in water (0.5 ml) was added immediately to the deep green solution to give a green precipitate. The suspension was heated under reflux (30 min), left to cool to room temperature and the leafy green crystalline solid filtered off and recrystallised promptly from ethanol to yield 15 as green plates. Yield=45 mg (40%). Mp=184° C.

Microanalysis: Calcd for $C_{29}H_{34}O_5N_2V$: C, 64.32; H, 6.32; N, 5.17. Found: C, 63.99; H, 6.40; N, 5.05.

MS (EI): m/z 541 ($M^+$).

Hydrosilylation Reactions

Hydrosilylations were carried out at room temperature using bis(divinyltetramethyldisiloxane) platinum(0) (Karsted catalyst; Fluorochem) as catalyst in sodium dried, thiophene-free toluene (Fluka). The siloxanes used were either prepared according to literature procedures (Akademie der Wissenschaften der DDR. Inv. EP-A 0348705, 1990, D. Hoebbel, I. Pitsch, W. Hiller, S. Schein; Chem. Abstr. 1990, 113, 125354b; Wacker-Chemie GmgH, Inv. EP-A 0367222, 1990, R. Weidner. N. Zeller, B. Deubzer, V. Frey; Chem. Abstr. 1990, 113, 116465m and M. Moran, C. M. Casado, I. Cuadrado, J. Losada; *Organometallics*, 1993, 12, 4327.), or purchased from commercial sources. Aliquots were withdrawn from the reaction mixtures at regular intervals and checked by IR spectroscopy for the disappearance of the Si—H stretch at 2165 $cm^{-1}$.

Octa({[8-(3-(10-decyloxydimethylsiloxy)-6-hydroxyphenyl)-2-phenyl-4,7-diazocta-1,3,7-trienato](2-) nickel (II)})octasilsexquioxane, (16)

Nickel(II) complex 9 (0.5105 g, 1.01 mmol) was added to a toluene solution (50 ml) containing 10 µl of a 3–3.5% solution of bis(divinyltetramethyldisiloxane)platinum(0) in xylene, and the whole was stirred (1 h) at room temperature. A gentle stream of air was blown through the red solution for a few seconds. A solution of octa(hysrodimethylsiloxy) octasilsexquioxane (Akademie der Wissenschaften der DDR, Inv. EP-A 0348705, 1990, D. Hoebbel, I. Pitsch, W. Hiller, S. Schein; Chem. Abstr. 1990, 113, 125354b; Wacker-Chemie GmgH, Inv. EP-A 0367222, 1990, R. Weidner. N. Zeller, B. Deubzer, V. Frey; Chem. Abstr. 1990, 113, 116465m and M. Moran, C. M. Casado, I. Cuadrado, J. Losada; *Organometallics*, 1993, 12, 4327.),(0.1017 g, 0.10 mmol) in toluene (20 ml) was added dropwise over a period of 2 h. A brown-red solid esparated as the addition progressed. After a further 1 h, the IR spectrum of the reaction mixture showed complete conversion (no Si—H peak was detected). At this point a few crystals of triphenylphosphine were added to deactivate the catalyst. The ochre-red solid was filtered off and dried in vacuo. The solid was washed with tetrahydrofuran to remove any unreacted monomer, dissolved in dichloromethane (5 ml) and filtered through a pasteur pipette loaded with Hyflo (filter aid) to remove any platinum(0) residues. The product was precipitated out of solution by addition to rapidly stirred methanol (750 ml). This procedure was repeated again until the solution showed no detectable amount of monomer by TLC. The ochre-red solid was filtered off and dried in vacuo. Yield=0.2717 g (53%). Mp=219° C. (dec.).

Microanalysis. Calcd for $C_{249}H_{328}O_{44}N_{16}Si_{16}Ni_{16}$: C, 56.97; H, 6.52; N, 4.42. Found: C, 55.39; H, 6.38; N, 4.42.

MS (FAB): m/z no $M^+$ detected; Ni—Si containing clusters of lower fragments.

GPC ($CHCl_3$, polystyrene standard): 5775 ($M_W$) and a second band at 2 $M_W$. $M_n$=5075; $M_W/M_n$=1.13. GPC analysis was performed by Raychem Corporate Technology Europe.

IR (KBr disc; υ, $cm^{-1}$): 1607 (vs, sharp; C=N, C=O and C=C—N coordinated); 1085 (vs, broad; Si—O—Si).

$^1H$ NMR ($CD_2Cl_2$): δ 7.11 (m, 8H; aromatic $C_6H_5$, HC=N, HC=C and NCH=C); 6.83 (m, 1H, $H_b$); 6.68 (m, 1H, $H_a$); 6.38 (m, 1H, $H_c$); 3.74 (t(J=7 Hz) 2H, $CH_2O$); 3.30 (S, 4H, N—$CH_2$); 1.68 (m, 2H, $CH_2$—$CH_2$—O); 1.30 (m, 14H, —($CH_2$)$_7$—); 0.60 (t(J=7 Hz) 2H, $CH_2$—Si); 0.13(, 6H, Si—$CH_3$).

$^{29}Si\{^1H\}$NMR ($CDCl_3$; Cr(acac)$_3$): δ 12.65 (s, Si($CH_3$)$_2$ $CH_2$,M silicon); –108.8 (s, $SiO_3$; Q silicon).

1,3,5,7-[Tetramethyl(tetra({[8-(3-(10-decyloxy)-6-hydroxyphenyl)-2-phenyl-4,7-diazocta-1,3,7-trienato](2-) nickel(II)}]cyclotetrasiloxane, (17)

Nickel(II) complex 9 (0.180 g, 0.356 mmol) was dissolved in toluene (20 ml) in a Schlenck tube under a nitrogen atmosphere and 10 µl of a 3–3.5% solution of Karsted catalyst was added. The red solution was stirred (1 h) at room temperature and a solution of 1,3,5,7-tetramethyl-cyclotetrahydrosiloxane (15.10 mg, 0.062 mmol) in toluene (6 ml) was added dropwise over a period of 1 h. During this time, a fine powder separated out. IR spectral monitoring of the rection mixture showed near complete conversion in 1 h. The suspension was stirred (18 h) at room temperature, the solid filtered off, dissolved in $Cl_2CH_2$ (5 ml) and the solution passed down a short pasteur pipette charged with Hyflo (filter aid). The compound was precipitated by addition to methanol (200 ml). This procedure was repeated again, affording 17 as an ochre-green powder. Yield=76.6 mg (54%). Mesomorphism: K 196 $S_A$ 296 Iso (° C.).

Microanalysis: Calcd for $C_{116}H_{152}O_{16}N_8Ni_4Si_4$: C, 61.61; H, 6.76; N, 4.95. Found: c, 59.83; H, 6.78; N, 4.70.

MS (FAB, NOBA matrix): m/z 2277, (cluster of $Si_4Ni_4$; $M^++OH$; ring opening); 2260 ($M^+$); 1785 ($M^+$-[Ni core-[O ($CH_2$)$_8$—H]); 1771 ($M^+$-[Ni core-[O($CH_2$)$_9$—H]); 1755 ($M^+$-[Ni core-[O($CH_2$)$_{10}$—H]).

$^1H$ NMR($CH_2Cl_2$): δ 7.10 (m, 8H, aromatic Ph, HC=N, HC=O, N—CH=C); 6.84 (m, 1H, $H_b$); 6.69 (m, 1H,$H_a$); 6.39 (m, 1H,$H_c$); 3.77 (t(J=7 Hz), 2H, $CH_2$—O—); 3.31 (s, 4H, $CH_2$—N); 1.69 (m, 2H, $CH_2$—O); 1.30 (m, 14H, —($CH_2$)$_7$—); 0.52 (m, 2H, $CH_2$—Si); 0.04 (m, 3H, $CH_3$—Si).

IR (KBr disc. υ $cm^{-1}$): 1607 (vs, sharp; C=N, C=O and C=C—N coordinated); 1082 (vs, broad; Si—O—Si).

$^{29}Si\{^1H\}$NMR ($CDCl_3$; Cr(acac)$_3$): δ –20.22 (s), –20.32 (s), –20.40 (s), –20.60 (s), (Si($CH_3$)$CH_2$—, geometric isomers).

[8-(2-hydroxy-5-(10-Pentamethyldisiloxydecyloxy) phenyl)-2-phenyl-4,7-diazocta-1,3,7-trienato](2-) nickel(II), (18)

10 µl of 3–3.5% solution of Karsted catalyst in xylene was added to a solution of nickel(II) complex 9 (0.1731 g, 0.342 mmol) in toluene (8 ml) under a nitrogen atmosphere. The solution was stirred (1 h) at room temperature and a solution of pentamethylhydrodisiloxane (Fluorochem) (44.1 mg, 0.297 mmol) in toluene (5ml) was added dropwise over a period of 1 h. IR spectral monitoring of the reaction showed complete dissapearance of the Si—H band in 2–4 h. The red solution was stirred overnight and the solvent removed in vacuo. The residue was dissolved in $CH_2Cl_2$ (5 ml), passed down a short pasteur pipette loaded with Hyflo (filter aid) and the red solution layered with methanol (80 ml) to yield red-brown needles which were recrystallised from $CH_2Cl_2$/MeOH once more to afford 18 as red-brown needles. Yield= 0.14 g (72%). Mesomorphism: K 164 K' 184 $S_A$ 240 Iso (° C.).

Microanalysis: Calcd for $C_{33}H_{50}O_4N_2Ni_1Si_2$: C, 60.64; H, 7.70; N, 4.28. Found: C, 62.01; H, 7.55; N, 4.39.

MS (EI): m/z 652 ($M^+$-1); 504 ($M^+$—$(CH_3)_3Si$—O—Si$(CH_3)_2$); 365 ($M^+$—$(CH_3)_3Si$—O—Si$(CH_3)_2C_{10}H_{20}$); 349 ($M^+$—$(CH_3)_3Si$—O—Si$(CH_3)_2C_{10}H_{20}O$).

IR (KBr disc; $\upsilon$, $cm^{-1}$): 1608 (vs, sharp; C=N, C=O and C=C—N coordinated); 1057 (vs, broad; Si—O—Si).

$^1H$ NMR($CD_2Cl_2$): δ 7.43 (s, 1H), 7.28 (m, 3H), 7.14 (m, 4H, aromatic Ph, HC=N, HC=O, N—CH=C); 6.87 (d($J_{ab}$=9 Hz)d($J_{bc}$=3 Hz), 1H, $H_b$); 6.71 (d($J_{ab}$=9 Hz), 1H, $H_a$); 6.54 (d($J_{bc}$=3 Hz) 1H, $H_c$); 3.80 (t(J=6 Hz) 2H, $CH_2O$); 3.30 (m, 4H, $CH_2N$); 1.69 (m, 2H, $CH_2$—$CH_2O$); 1.30 (m, 14H, $(CH_2)_7$); 0.49 (m, 2H, $CH_2$—Si); 0.04 (s, 9H, $(CH_3)_3$Si—O); 0.01 (s, 6H, $CH_2$—$(CH_3)_2$—Si—O).

Methyl 2-(4-undec-10-enyloxyphenyl) ethanoate, (19)

A solution of methyl (4-hydroxyphenyl)ethanoate (7.50 g, 45 mmol)1-bromoudec-10-ene (10 g, 43 mmol) and potassium carbonate (7.50 g, 54 mmol) in butanone (250 ml) was heated under reflux (12 h). The solvent was removed in vacuo to yield a pale yellow oil.

2-Undec-10-enyloxyphenyl)ethanoic acid, (20)

A solution of 19 (12.49 g, 39 mmol) in ethanol (100 ml) was hydrolysed with sodium hydroxide (25% aqueous solution, 60 ml) and the reaction mixture stirred and heated under reflux (1 h). After cooling to room temperature, the solution was acidified with concentrated hydrochloric acid to give the free carboxylic acid which was recrystallised from ethanol. Yield=13.40 g (100%).

2-(4-Undec-10-enyloxyphenyl)-N,N-dimethyl-1-aminoprop-1-en-3-al, (21)

DMF (12.0 ml, 154 mmol) was cooled to 0° C. under an atmosphere of dry nitrogen and phosphoryl chloride (8.98 ml, 99 mmol) was added dropwise, whilst maintaining the temperature below 5° C. The reaction mixture was stirred for a further 10 minutes after the addition was complete. A solution of 20 (10.0 g, 33 mmol) in DMF (10.0 ml) and added dropwise and the reaction mixture heated under nitrogen at 70° C. with stirring (20 h) to yield a dark brown solution. After cooling, the reaction mixture was poured onto ice (150 g) and neutralized by the addition of potassium carbonate. Sodium hydroxide solution (22 g in 22 ml water) was added and a brown oil separated from the aqueous layer. The oil was extracted into diethyl ether and dried ($MgSO_4$). The diethyl ether was removed in vacuo to give a brown oil. Yield=11.17 g (98%).

2-(4-Alkoxyphenyl)-and 2-(4(alk-ω-enyloxy)phenyl)-3-hydroxyprop-2-enals were prepared from the corresponding 4-alkoxy- or 2-(4-alk-ω-enyloxyphenyl)acetic acids by the same procedure. The latter were prepared by standard alkylation of 4-hydroxyphenylacetic acid (Aldrich) with n-alkyl bromides (Aldrich) or ω-alkenyl bromides (Lancaster). For Example:

2-(4-undec-10-enyloxyphenyl)-1-hydroxyprop-1-en-3-al, (22)

A solution of 21 in ethanol (75 ml) was hydrolysed with aqueous sodium hydroxide solution (60 ml, 25%). The reaction mixture was stirred and heated under reflux (3 h), cooled to room temperature and the ethanol removed in vacuo to yield an off-white solid which was filtered and washed thoroughly with water. The solid was suspended in a 50% ethanol/water mixture (150 ml) and acidified with concentrated hydrochloric acid. The suspended solid whitened in colour and was collected by filtration, then recrystallised from petroleum ether (bp 60–80° C.). Yield=3.97 g (38%).

8-(2-Hydroxy-5-octyloxyphenyl)-2-(4-undec-10-enyloxyphenyl)-4,7-diazocta-2,7-dien-1-al, (24)

1,2-Diaminoethane (0.23 g, 3.8 mmol) was added dropwise to a solution of 22 (1.20 g, 3.8 mmol) in dichloromethane (250 ml) to give a precipitate which gradually redissolved with stirring. 2-Hydroxy-5-octyloxybenzaldehyde (3b) (0.91 g, 3.8 mmol) was added to the reaction mixture which was stirred and heated under reflux (48 h). After cooling, the dichloromethane was removed in vacuo, to give a bright yellow solid. TLC (silica gel, DCM/$Et_2O$, 3:2) showed three spots corresponding to 23, 24 and 25. The solid was dissolved in the minimum amount of dichloromethane and purified by column chromatography (silica gel, dichloromethane/diethyl ether, 3:2). Two of the fractions were isolated pure as follows:

24: $R_f$=0.39; Yield=0.56 g, (28%). Mp=136° C.

25: $R_f$=0.70; Yield=0.23 g, (11%). Mp=122° C.

Spectral and Analytical Data for 24:

$^1H$ NMR($CD_2Cl_2$): δ 12.43 (1H, S, OH); 10.32 (1H, M, NH); 9.41 (1H, d, J=2 Hz, CHO); 8.30 (1H, s, CHN); 7.04-6.74 (8H, m, aromatic H and CHNH); 5.81 (1H,=CH, d, $J_{trans}$=17 Hz; d, $J_{cis}$=10 Hz; t, $J_{HCH2}$=6 Hz); 4.99 (1H, $CH_2$=d($J_{trans}$=17 Hz)m); 4.92 (1H, $CH_2$=, d($J_{cis}$=10 Hz)m); 3.90 (4H, m, $CH_2O$—); 3.79 (2H, m, $CH_2$—NH—); 3.62 (2H, m, $CH_2$—N=); 2.05 (2H, m, aliphatic H); 1.75 (4H, m, aliphatic H); 1.30 (22H, m, aliphatic H); 0.90 (3H, t,J=7 Hz,$CH_3$).

1,6-Di(2-hydroxy-5-undec-10-enyloxyphenyl)-2,5-diazahexa-1,5-diene, (26)

A solution of 2-hydroxy-5-undec-10-enyloxybenzaldehyde (3c) (1.48 g, 5.1 mmol) and 1,2-diaminoethane (0.34 ml, 5.1 mmol) in ethanol (200 ml) was stirred and heated under reflux (1 h). The ethanol was removed in vacuo to give a yellow solid which was recrystallised from petroleum ether (bp 60–80°). Yield=0.84 g (27%). Mp=108° C.

Microanalysis: Calcd for $C_{38}H_{56}N_2O_4$: C, 75.46; H, 9.37; N, 4.63. Found: c, 75.57; H, 9.37; N, 4.45.

$^1H$ NMR($CDCl_3$): δ 12.68 (1H, s, —OH), 8.29 (1H, s, CHN); 6.93-6.71 (3H, m, aromatic-H), 5.81 (1H,=CH, d, $J_{trans}$=17 Hz; d, $J_{cis}$=10 Hz; t, $J_{HCH2}$=6 Hz); 4.99 (1H, $CH_2$=, d ($J_{trans}$=17 Hz), m; 4.90 (1H, $CH_2$=, d,$J_{cis}$=5 Hz); 3.94 (2H, s, $CH_2N$=C); 3.87 (2H, t, $CH_2O$, J=6 Hz); 2.04 (2H, m, aliphatic-H); 1.73 (2H, m, aliphatic-H); 1.30 (12 H, m, aliphatic-H).

IR (KBr disc, υ cm$^{-1}$): 2960(s), 2925(m), 1585(w), 1488 (w), 1468(m), 1390(w), 1328(w), 1272(s), 1228(w), 1165 (m), 1040(m) 1020(m), 910(w), 850(w), 825(w).

[1,6-Di(2-hydroxy-5-undec-10-enyloxyphenyl)-2,5-diazahexa-1,5-dienato](2-) nickel(II), (27)

Nickel(II) acetate tetrahydrate (0.35 g, 1.40 mmol) was added to a solution of 26 (0.84 g, 1.40 mmol) in ethanol (50 ml) and the reaction mixture was heated under refluxed (1 h), causing a colour change from yellow to red. On cooling, a crystalline solid was obtained which was recrystallised from dichloromethane and ethanol to give brown/gold needles. Yield=0.94 g (100%). Mesomorphism: K 148 $S_A$ 248.9 Iso Microanalysis: Calcd for $C_{38}H_{54}N_2O_4Ni$: C, 69.00; H, 8.24; N, 4.24. Found: C, 67.57; H, 8.12; N, 4.08.

1. $^1$H NMR(CDCl$_3$): δ 7.22 (1H, s, CHN); 6.94-6.84 (2H, m, aromatic-H); 6.35 (1H, d, aromatic-H, J=2 Hz), 5.81 (1H, =CH, d, J$_{trans}$=17 Hz; d,J$_{cis}$=10 Hz; t, J$_{HCH2}$=6 Hz); 4.99 (1H, CH$_2$=d, J$_{trans}$=17 Hz; 4.92 (1H, CH$_2$=, d, J$_{cis}$=10 Hz); 3.79 (2H, t, —CH$_2$O, J=7 Hz); 3.42 (2H, s, CH$_2$—N); 2.04 (2H, m, aliphatic-H); 1.71 (2H, m, aliphatic-H); 1.30 (12H, m, aliphatic-H). All integrations halved due to plane of symmetry (See for example, K. Miyamura et al., *Bull. Chem. Soc. Jpn.*, 1989, 45).

$^{13}$C NMR(CDCl$_3$,Si(CH$_3$)$_4$): δ 161, 160 (aromatic, C—O); 148 (Ar—*C=N); 139 (aromatic *C—C=N); 124, 122, 119 (aromatic); 114 (H$_2$C*=C); 113 (—CH$_2$C*H=); 76 (—*CH$_2$—O—Ar); 68 (CH$_2$N=C); 34 (—C*H$_2$CH$_2$OAr); 30.0, 29.6, 29.5, 29.2, 29.0, 26.0 (7×CH$_2$).

[1,6-Di(2-hydroxy-5-(11-pentamethyldisiloxyundecyloxy)phenyl)-2,5-diazahexa-1.5-dienato](2-) nickel(II), (28)

Hexachloroplatinic acid (50 μl, 2.44×10$^{-5}$ M in Bu$^t$OH, 1.22×10$^{-4}$ mmol) was added to a solution of 11 (0.34 g, 0.51 mmol) and pentamethyldisiloxane (0.17 g, 1.15 mmol) in dry toluene (10 ml) under an atmosphere of dry nitrogen and the reaction mixture heated with stirring at 60° C. The progress of the reaction was monitored by TLC (silica gel, DCM/ethyl acetate, 9/1). After 7 days, TLC indicated that only a trace of the starting material remained. The reaction mixture was cooled to room temperature and the toluene removed in vacuo to yield a brown solid which was dissolved in dichloromethane, filtered and taken to dryness. The crude product was recrystallised from ethanol to give a brown waxy solid. Yield=0.14 g, (29%). Mesomorphism: K 115.8 $S_A$ 218.0 Iso (° C.).

Microanalysis: Calcd for $C_{48}H_{86}N_2O_6Si_4Ni$: C, 59.19; H, 8.91; N, 2.88. Found C, 61.02; H, 8.87; N, 3.08.

$^1$H NMR(CDCl$_3$): δ 7.30 (1H, s, CHN); 6.97-6.86 (2H, m, aromatic-H): 6.42 (1H, d, aromatic-H, J=3 Hz); 3.81 (2H, t, CH$_2$O—, J=7 Hz), 3.42 (2H, s, —CH$_2$N—); 1.70 (2H, m, aliphatic-H); 1.25 (16H, m, aliphatic-H); 0.50 (2H, m, CH$_2$—Si); 0.05-0.03 (15H, s, Si—CH$_3$). All integrations halved, plane of symmetry.

IR (KBr disc, υ cm$^{-1}$); 2977(m), 2958(s), 2922(s), 1622 (s), 1608(m), 1530(m), 1460(s), 1430(m), 1305(m), 1120 (m), 1170(m), 1060(m), 840(s), 810(m).

[8-(2-Hydroxy-5-octoxyphenyl)-2-(4-undec-10-enyloxyphenyl)-4,7-diazocta-1,3,7-trienato](2-) nickel(II), (29a)

Nickel(II) acetate tetrahydrate (0.13 g, 0.54 mmol) was added to a solution of 24 (0.30 g, 0.54 mmol) in ethanol (100 ml) and the reaction mixture stirred and heated under reflux (1 h). The resulting solution was cooled and the ethanol removed in vacuo to yield a green/gold metallic solid which was recrystallised from ethanol. Yield=0.14 g (41%). Mesomorphism: K 187 $S_A$ 266 Iso ° C.

$^1$H NMR(CDCl$_3$): δ 7.40-6.74 (8H, m, H aromatic-H and CHNH); 5. (1H, =CH, d, J$_{trans}$=17 Hz; d, J$_{cis}$=10 Hz; t, J$_{HCH2}$=6 Hz); 4.99(1H, CH$_2$=d, J$_{trans}$=17 Hz; 4.92 (1H, CH$_2$=, d, J$_{cis}$=10 Hz); 3.90 (4H, m, —CH$_2$O—, J=6 Hz); 3.79, (2H, m, CH$_2$—NH—); 3.62 (2H, m, CH$_2$—N=_; 2.05 (2H, m, aliphatic-H); 1.75 (4H, m, aliphatic-H); 1.30 (22H, m, aliphatic-H); 1.30 (3H, t,CH$_3$, J=3 Hz).

[8-(2-Hydroxy-5-octyloxy)-2-(4-undec-10-enyloxyphenyl)-4,7-diazaocta-1,3,7-trienato (2-)] copper(II), (29b)

A suspension of copper acetate monohydrate (34 mg, 0.169 mmol) in methanol (5 ml) was added to a hot solution of 24 (0.10 g, 0.169 mmol) in methanol (15 ml). The violet-green solution was heated under reflux (1 h) and on cooling to room temperature produced brown-green crystals which were filtered off and recrystallised from CH$_2$Cl$_2$/MeOH, to afford 29b as brown-violet needles. Yield=85 mg (77%). Mesomorphism: K 163.7 $S_A$ 195 Iso (dec).

Microanalysis: Calcd for $C_{37}O_{52}O_4N_2Cu$. 0.5CH$_2$Cl$_2$: C, 64.82; H, 7.68; N, 4.03. Found: C, 64.77; H, 7.76; N, 4.05.

MS (EI): m/z 652 (M$^+$).

IR (KBr disc; v cm$^{-1}$); 1626 (vs), 1610 (sh), CO and CN co-ordinated.

Molecular weight determination (CHCl$_3$): Calcd for $C_{37}O_{52}O_4N_2Cu$: 652.31. Found: 652

[8-(2-Hydroxy-5-octoxyphenyl)-2-(4-(11-pentamethyldisiloxyundecyloxy)phenyl)-4,7-diazocta-1,3,7-trienato](2-) nickel(II), (30)

Hexachloroplatinic acid (50 μl. 2.44×10$^{-5}$ M in BuOH. 1.22×10$^{-4}$ mmol) was added to a solution of 29 (0.14 g, 0.22 mmol) and pentamethyldisiloxane (0.04 g, 0.27 mmol) in dry toluene (10 ml) and the reaction mixture heated with stirring under nitrogen (60° C./7 days). The toluene was removed in vacuo to give a brown solid which was dissolved in dichloromethane, filtered and taken to dryness. The crude product obtained was recrystallised from ethanol to give a brown waxy solid. Monosilylation was confirmed by $^1$H NMR. Yield=0.11 g (60%). Mesomorphism: K 188 $S_A$ 259 Iso ° C.

Microanalysis: Calcd for $C_{42}H_{69}N_2O_5Si_2Ni$: C, 62.69; H, 8.64; N, 3.48. Found C, 63.72; H, 8.34; N, 3.62.

$^1$H NMR(CDCl$_3$): δ 7.44 (1H, s, CHO, delocalised); 7.32 (1H, s, CHN, delocalised); 7.07-6.82 (7H, m, aromatic-H); 6.53 (1H, s, CHN); 3.93 (2H, t, CH$_2$O, J=7 Hz); 3.83 (2H, t, CH$_2$O, J=7 Hz); 3.33 (4H, m, CH$_2$N); 1.70 (2H, m, CH$_2$); 1.30 (28H, m, aliphatic-H); 0.89 (3H, m, aliphatic-H); 0.50 (2H, m, CH$_2$—Si); 0.15 (15H, m, Si—CH$_3$).

IR (KBr disc, υ cm$^{-1}$): 2978(m), 2960(s), 2925(s), 1608 (m), 1530(m), 1508(m), 1470(m), 1460(s), 1320(m), 1305 (m), 1270(m), 1250(m), 1240(m), 1070(m), 1050(s,b), 835 (s).

8-(2-hydroxy-5-undec-10enlkoxyphenyl)-2-(4-decyloxyphenyl)-4,7-diazocta-2,7-dien- 1-al, (32).

3-Ethoxy-2-(4-undecyloxyphenyl)prop-2-enal (31) (1.263 g, 3.8 mmol) was dissolved in dichloromethane (250 ml). A solution of 2-hydroxy-5-undec-10- enyloxybenzaldehyde (3c) (1.103 g, 3.8 mmol) in dichloromethane (10 ml) was added to the reaction mixture which was heated under reflux (72 h) to give a yellow solution. The reaction mixture was cooled to room temperature and the composition analysed by TLC (silica gel, DCM/Et$_2$O, 3/2). The solution was taken to dryness in vacuo to yield a yellow solid which was dissolved in the minimum amount of dichloromethane and purified by column chromatography (silica gel, DCM/Et$_2$O, 3/2) to afford two fractions.

32: R$_f$=0.30. Yield=0.06 g (3%). Mp=102° C.

33: R$_f$=0.70. Yield=0.73 g (20%).

Spectral and Analytical Data for 32:

$^1$H NMR(CDCl$_3$): δ 12.45 (2H, s, enolic-OH): 10.36 (1H, m, NH); 9.41 (1H, CHO, d(J=2 Hz)); 8.30 (1H, s, CHN); 7.20-6.75 (8H, m, aromatic-H); 5.81 (1H, =CH,d,(Jtrans=13 Hz), d,(Jcis=5 Hz), T, (JHCH$_2$=3 Hz)); 4.99 (1H, CH$_2$=, d, (Jtrans=13 Hz)); 4.92 (1H, CH$_2$=, d, (Jcis=5 Hz)); 3.89 (4H, m, CH$_2$O); 3.79 (2H, m, CH$_2$NH); 3.62 (2H, m, CH$_2$N=C); 2.04 (2H, m, aliphatic-H); 1.75 (4H, m, aliphatic-H); 1.30 (26H, m, aliphatic-H); 0.85 (3H, m, CH$_3$).

Poly{Dimethylsiloxy|8-(2-hydroxy-5-octyloxy)-2-(4-(undec-11-yloxy)phenyl)-4,7-diazaocta-1,3,7-trienato (2-)|copper(II)}, (33)

A solution of poly(dimethylhydrosiloxane) (Petrarch PS 119; 22.05 mg, 0.367 mmol) in toluene (3 ml) was added to a Schlenk tube containing 29b (0.2660 g, 0.407 mmol) in toluene (15 ml) under nitrogen atmosphere. The platinum catalyst (Wacker Platinum catalyst SLM 86003; 11 μl) was added and the solution heated to 100° C. When the reaction had proceeded to completion (as determined by IR spectroscopy) the solvent was evaporated in vacuo and the brown residue dissolved in CH$_2$Cl$_2$ (15 ml), filtered through Hyflo (filter aid), and precipitated by slow addition to methanol (250 ml) with vigorous stirring. The suspension was stirred (1.5 h) and the solid recovered by centrifugation. collected and dried in air; this procedure was repeated twice, affording yield: 795 mg, 30%. Mesomorphism: K 177 SA 192 (dec).

IR(KBr disc; v cm$^{-1}$): 1626 (vs), 1610 (sh). CO and CN coordinated. Soluble in CHCl$_3$ indicating no cross-linking.

ACRYLATE AND METHACRYLATE COMPLEXES

11-Bromo-1-tetrahydropyranyloxyundecane (34)

50 g (0.199 mol) of 11-bromo-1-undecanol (Aldrich) was dissolved in 500 ml of dichloromethane, and the mixture was cooled to 0° C. 22.15 ml (0.242 mol) of dihydropyran were added dropwise over a period of two hours; the reaction was started by addition of a few crystals of p-toluenesulphonic acid at the beginning of the addition. After the addition was complete, the reaction mixture was stirred for 15 min and stopped by addition of 0.5 g of NaHCO$_3$. After evaporation of the dichloromethane, the pale yellow syrup obtained was dissolved in ethyl acetate and purified by filtration through silica gel. Yield=65.3 g (98%).

4-(11-Tetrahydropyranyloxyundecyloxy)phenol (35)

4.72 g (65 mmol) of KOH was dissolved in 300 ml of absolute ethanol under a nitrogen atmosphere and 19.5 g (177 mmol) of hydroquinone were added. The mixture was heated under reflux and a solution of 19.81 g (59 mmol) 11-Bromo-1-tetrahydropyranyloxyundecane in 50 ml of ethanol was added dropwise. The reaction mixture was boiled for 20 h, then the solvent was evaporated off and the residue extracted with diethyl ether (3×300 ml), washed with saturated aqueous NaCl (150 ml) and dried over MgSO4. The solvents were evaporated under vacuum and the residue extracted with n-heptane to afford a first crop of pure phenol. The rest of the crude material was purified by column chromatography over flash grade silica gel (diethyl ether/hexane, 2/3; R$_f$=0.27). Yield=12.65 g (59%).

$^1$H NMR (CDCl$_3$): d 6.76 (m, 4H, aromatic C$_6$H$_4$); 4.90 (s,1H, OH); 4.60 (m, 1H, CHO—CH$_2$ THPO); 3.89 (t, J=7 Hz), 2H, CH$_2$O); 3.74, 3.52, 3.40 (m, 4H, CH$_2$O THPO); 1.75–1.50 (m, 4H, CH$_2$—CH$_2$—O); 1.30 (m, 20H, (CH$_2$)).

2-Hydroxy-5-(11-tetrahydropyranyloxyundecyloxy)benzaldehyde (36)

Tin tetrachloride (0.23 ml, 2.0 mmol) was added to a solution of tetrahydropyranyloxyphenol (7.35 g, 20.0 mmol) in sodium dried, degassed toluene (250 ml) under a nitrogen atmosphere. Tri-n-butylamine (1.90 ml, 8.0 mmol) was added at room temperature. The solution turned yellow and was stirred for 1 h before paraformaldehyde (BDH) (1.32 g, 44 mmol) was added and the yellow suspension heated to 105° C. (3 h). The brown solution was cooled, poured onto saturated aqueous NaCl (200 ml) and acidified to pH 2 with 10% HCl. The product was extracted with ether (3×100 ml) and the combined organic layers dried over MgSO$_4$ and evaporated. The residue was purified by column chromatography (flash grade silica gel; petroleum ether 40–60° C./diethyl ether, 1/1). The salicylaldehyde was isolated as a yellow solid (R$_f$=0.45). Yield=2.79 g (36%).

$^1$H NMR (CDCl$_3$): d 10.64 (s, 1H, OH); 9.85 (s, 1H, CHO); 7.20–6.80 (m, 4H, aromatic C$_6$H$_4$); 4.60 (m, 1H, CHO—CH$_2$ THPO); 3.93 (t, J=7 Hz), 2H, CH$_2$O); 3.74, 3.52, 3.38 (m, 4H, CH$_2$O THPO); 1.80–1.50 (m, 4H, CH$_2$—CH$_2$—O); 1.30 (m, 20H, (CH$_2$)$_{10}$).

8-(3-(11-Tetrahydropyranyloxyundecyloxy)-6-hydroxyphenyl)-2-phenyl-4,7-diazocta-2,7-dien-1-al (37)

1,2-Diaminoethane (0.25 ml; 3.87 mmol) was added to a vigorously stirred solution of phenylmalonaldehyde (0.573 g; 3.87 mmol) in dichloromethane (350 ml). A white precipitate formed immediately.

5-(Tetrahydropyranyloxyundecyloxy)salicylaldehyde (1.520 g; 3.87 mmol) was added and the resulting yellow suspension stirred at room temperature for 18 h and refluxed using a Dean-Stark apparatus until a clear yellow solution was obtained (approximately 6 h). The yellow solution was evaporated in vacuo and the residue purified by column chromatography (flash grade silica gel, Cl$_2$CH$_2$/THF, 4/1). The band with R$_f$=0.75 yielded symmetrical salen derivative. The band with R$_f$=0.50 was collected and the product recrystallised from hot MeOH to yield yellow microcrystals of 37. Yield=0.371 g (34%).

Microanalysis: Calcd for C$_{34}$H$_{48}$O$_5$N$_2$: C, 72.31; H, 8.56; N, 4.95. Found: C, 72.33; H, 8.77; N, 5.03.

MS (EI): m/z 565 (M$^+$); 480 (M$^+$-THP).

$^1$H NMR (CDCl$_3$): δ 12.44 (s, 1H, OH); 10.49 (m broad, 1H, NH); 9.47 (d, J=4 Hz, 1H, CHO); 8.31 (s, 1H, CH=N); 7.30–6.75 (m, 9H, aromatic C$_6$H$_4$, NCH=C); 4.58 (m, 1H, CHO—CH$_2$ THP); 3.88 (t, J=7 Hz), 2H, CH$_2$O); 3.87–3.34 (m, 4H, CH$_2$—N=CH and CH$_2$—NH; 4H, CH$_2$O THP); 1.80–1.50 (m, 4H, CH$_2$—CH$_2$—O); 1.30 (m, 20H, (CH$_2$)).

[8-(3-(11-Tetrahydropyranyloxyundecyloxy)-6-hydroxyphenyl)-2-phenyl-4,7-diazocta-1,3,7-trienato](2-)nickel(II) (38)

Nickel acetate tetrahydrate (110.1 mg; 0.44 mmol) was added to a solution of the tetrahydropyranyloxy ligand (0.250 g; 0.44 mmol) in 20 ml of methanol previously heated to reflux. Red microcrystals formed immediately. The suspension was heated 1 h to reflux. After cooling to room temperature, the red-brown needles formed were filtered off and recrystallised from methanol. Yield=0.210 g (76%).

Mesomorphism: K (134 SmA) 158 Iso ° C.

Microanalysis: Calcd for $C_{34}H_{46}O_5N_2Ni$: C, 65.71; H, 7.45; N, 4.50. Found: C, 64.99; H, 7.61; N, 4.31.

MS (EI): m/z 621 (M$^+$); 593 (M$^+$—CHO); 536 (M$^+$-THP), 365 (M$^+$-THP-$(CH_2)_{11}$O) IR (KBr disc,u cm$^{-1}$): 1609 (vs, sharp; C=N, C=O and C=C—N coordinated).

$^1$H NMR (CDCl$_3$): d 7.45–7.10 (m, 8H; aromatic $C_6H_4$, HC=N, HC=O and NCH=C); 6.93 (s, broad, 2H, aromatic $C_6H_4$); 6.52 (m, 1H, H$_c$); 4.67 (m, 1H, CHO—CH$_2$ THP); 3.88 (t, J=7 Hz, 2H, CH$_2$O); 3.87–3.68 (m, 2H, CH$_2$O); 3.55–3.28 (4H CH$_2$—N=CH and CH$_2$—NH; 2H, CH$_2$O THP); 1.80–1.50 (m, 4H, CH$_2$—CH$_2$—O); 1.30 (m, 20H, (CH$_2$)$_{10}$).

[8-(3-(11-Hydroxyundecyloxy)-6-hydroxyphenyl)-2-phenyl-4,7-diazocta-1,3,7-trienato](2-)nickel(II) (39)

Tetrahydropyranyloxy protected nickel complex 38 (0.500 g; 0.848 mmol) was dissolved in Cl$_2$CH$_2$/MeOH 1/1 (20 ml) and p-toluenesulphonic acid monohydrate added (16 mg; 0.0848 mmol). The solution was heated to reflux in air (12 h) then cooled down, and the solvents evaporated. The residue was subjected to column chromatography on flash grade silica gel, eluting with Cl$_2$CH$_2$/THF 4/1. The alcohol-terminated nickel complex (R$_f$=0.33) was isolated as golden red needles from methanol (0.217 g). The isolated unreacted starting nickel complex (R$_f$=0.66) was subjected to hydrolysis as above to yield a second crop of the alcohol (0.089 g). Combined yield=0.300 g (85%).

Melting point=K 210 Iso ° C.

Microanalysis: Calcd for $C_{29}H_{38}O_4N_2Ni$: C, 64.83; H, 7.12; N 5.21. Found: C, 64.62; H, 7.05; N, 4.92.

MS (EI): m/z 536 (M$^+$-1).

IR (KBr disc,u cm$^{-1}$): 3423 (vs. broad; OH); 1606, 1592 (vs. sharp; C=N, C=O and C=C—N coordinated).

$^1$H NMR (CDCl$_3$): d 7.45–7.10 (m, 8H; aromatic $C_6H_4$, HC=N, HC=O and NCH=C); 6.93 (s, broad, 2H, aromatic $C_6H_4$); 6.53 (m, 1H, H$_c$); 3.83 (t, J=7 Hz, 2H, CH$_2$O-Ph); 3.65 (q broad, J=6 Hz, 2H, CH$_2$—OH); 3.40 (m, 2H, CH$_2$—N=CH); 3.31 (m, 2H, CH$_2$—NH); 1.73 (m, 2H, CH$_2$—CH$_2$—O); 1.30 (m, 16H, (CH$_2$)$_8$).

[8-(3-(11-Methacryloxyundecyloxy)-6-hydroxyphenyl)-2-phenyl-4,7-diazocta-1,3,7-trienato](2-) nickel(II) (40)

The alcohol-terminated nickel complex 39 (0.185 g, 0.345 mmol) was dissolved in 30 ml of sodium dried toluene under a nitrogen atmosphere. Methacryloyl chloride (0.033 ml, 0.345 mmol) was added and the solution stirred for 5 min; a few crystals of hydroquinone were added to stabilize the solution; triethylamine (0.048 ml, 0.345 mmol) was added and the red suspension stirred 18 h at room temperature. The solvent was evaporated in vacuo at room temperature and the residue purified by column chromatography (flash grade silica gel, Cl$_2$CH$_2$/THF 90/10) to yield red crystals of 40. Yield=0.124 g (60%).

Melting point=K 185 Iso ° C.

Microanalysis: Calcd for $C_{33}H_{42}O_5N_2Ni$: C, 65.47; H, 6.98; N, 4.62. Found: C, 65.31; H, 7.03; N, 4.53.

MS (EI): m/z 605 (M$^+$); 368 (M$^+$—(CH$_2$)$_{11}$OCOMeCH=CH$_2$).

IR (KBr disc,u cm$^{-1}$): 1710 (vs, sharp, COO); 1620 (sh), 1608 (vs. sharp; C=N, C=O and C=C—N coordinated).

$^1$H NMR (CDCl$_3$): d 7.45–7.10 (m, 8H; aromatic $C_6H_4$, HC=N, HC=O and NCH=C); 6.93 (s, broad, 2H, aromatic $C_6H_4$); 6.53 (m, 1H, aromatic $C_6H_4$); 6.10 (s, 1H, cis-CH=C(COO)); 5.55 (m, 1H, trans-CH=C(COO)); 4.14 (t, J=7 Hz, 2H, CH$_2$—OCO); 3.82 (t, J=7 Hz, 2H, CH$_2$O-Ph); 3.40 (m, 2H, CH$_2$—N=CH); 3.32 (m, 2H, CH$_2$—NH); 1.95 (s, 3H, CH$_3$—CH=); 1.70 (m, 2H, CH$_2$—CH$_2$—O); 1.30 (m, 16H, (CH$_2$)$_8$).

[8-(3-(11-Acryloxyundecyloxy)-6-hydroxyphenyl)-2-phenyl-4,7-diazocta-1,3,7-trienato](2-) nickel(II) (41)

The alcohol-terminated nickel complex 39 (0.300 g, 0.558 mmol) was dissolved in 30 ml of a mixture of sodium dried toluene and dichloromethane 1/1 under a nitrogen atmosphere. Acryloyl chloride (Fluka) (0.054 ml, 0.669 mmol) was added and the solution stirred for 5 min. Triethylamine (0.093 ml, 0.669 mmol) was added and a few crystals of hydroquinone were added to stabilize the solution. The red suspension was stirred 18 h at room temperature. The solvent was evaporated in vacuo at room temperature and the residue purified by column chromatography (flash grade silica gel, Cl$_2$CH$_2$/THF 90/10) to yield red crystals of 41. Yield=0.130 g (40%).

Microanalysis: Calcd for $C_{32}H_{40}O_5N_2Ni.1/2$ CH$_2$Cl$_2$: C, 61.59; H, 6.51; N, 4.41. Found: C, 60.78; H, 6.43; N, 4.37.

MS (EI): m/z 591 (M$^+$); 365 (M$^+$—(CH$_2$)$_{11}$OCOCH=CH$_2$).

IR (KBr disc,u cm$^{-1}$): 1710 (vs, sharp, COO); 1620 (sh), 1608 (vs. sharp; C=N, C=O and C=C—N coordinated).

$^1$H NMR (CDCl$_3$; 400 MHz): d 7.45–7.10 (m, 8H; aromatic $C_6H_4$, HC=N, HC=O and NCH=C); 6.93 (s, broad, 2H, aromatic $C_6H_4$); 6.53 (m, 1H, aromatic $C_6H_4$); 6.39 (d (J$_{trans}$=17 Hz) d(J$_{de}$=1 Hz), 1H, H$_e$); 6.12 (d(J$_{trans}$=17 Hz) d(J$_{cis}$=10 Hz), 1H, H$_f$); 5.81 (d(J$_{cis}$=10 Hz) d(J$_{de}$=1 Hz), 1H, H$_d$); 4.15 (t, J=7 Hz, 2H, CH$_2$—OCO); 3.82 (t, J=7 Hz, 2H, CH$_2$O-Ph); 3.39 (t, J=6 Hz, 2H, CH$_2$—N=CH); 3.30 (t, J=6 Hz, 2H, CH$_2$—NH); 1.95 (s, 3H, CH$_3$—CH=); 1.69 (m, 2H, CH$_2$—CH$_2$—O); 1.33 (m, 16H, (CH$_2$)$_8$).

POLYMERISATION REACTIONS

Polymerisation reactions were carried out in sodium/benzophenone-dried THF, using AIBN as radical initiator, under a nitrogen atmosphere. In both cases, the final polymer was precipitated from dichloromethane into a large volume of methanol with vigorous stirring. Absence of initial monomer was checked at this stage by thin layer chromatography. The polymers were recovered by filtration and dried under vacuum for several hours. Their $^1$H NMR spectra show broad, unresolved resonances, typical of polymers; the absence of unreacted monomer was confirmed in both cases.

Poly[8-(3-(11-Acryloxyundecyloxy)-6-hydroxyphenyl)-2-phenyl-4,7-diazocta-1,3,7-trienato](2-) nickel(II)] (42)

The acrylate monomer (84 mg; 0.142 mmol) and 66 μl of a solution of 0.1 g of AIBN in 10 ml of dry THF (ratio inititor/monomer=3 mol %) were placed in a Schlenck tube which was evacuated and filled with nitrogen several times. Freshly distilled dry THF (6 ml) was added and the solution subjected to three freeze-thaw cycles and flushed with nitrogen. The tube was placed in an oil bath at 70° C. to initiate the polymerisation. After 48 h the reaction solution was cooled down to room temperature where upon a fine ochre coloured solid precipitated out. The whole mixture was evaporated to dryness, the residue dissolved in 3 ml of $CH_2Cl_2$ and precipitated into 200 ml of methanol with vigorous stirring. This procedure was repeated once more, until the solid showed no trace of acrylate monomer by TLC. The red-ochre solid was filtered off and dried under vacuum. Yield=44 mg (53%).

Microanalysis: Calcd for $C_{32}H_{40}O_5N_2Ni$: C, 64.99; H, 6.81; N, 4.73. Found: C, 64.24; H, 6.96; N, 4.45.

IR (KBr disc,u $cm^{-1}$): 1710 (vs. sharp, COO); 1620 (sh), 1608 (vs, sharp; C=N, C=O and C=C—N coordinated).

$^1$H NMR ($CDCl_3$; 400 MHz): d 7.45–7.10 (m, 8H; aromatic $C_6H_4$, HC=N, HC=O and NCH=C); 6.89 (s, broad, 2H, aromatic $C_6H_4$); 6.40 (m, broad, 1H, aromatic $C_6H_4$); 4.05 (s, 2H, $CH_2$—OCO); 3.76 (s, br,2H, $CH_2$O-Ph); 3.34 (s, br, 4H, $CH_2$—N=CH, $CH_2$—NH); 2.51–2.00 (br, $CH_2$—CH—OCO); 1.84 (m, br, $CH_2$—CH—OCO); 1.69 (m, br, 2H, $CH_2$—$CH_2$—O); 1.60 (m, br, 2H, $CH_2$—$CH_2$—O); 1.33 (m, 16H, $(CH_2)_8$).

Poly[8-(3-(11-Methacryloxyundecyloxy)-6-hydroxyphenyl)-2-phenyl-4,7-diazocta-1,3,7-trienato](2-) nickel(II)] (43)

Polymer 43 was prepared following the procedure described above from the methacryloxy nickel complex (80 mg; 0.132 mmol) and AIBN (0.2 mg; 1 mol %) in THF (6 ml). Yield=50 mg (62%).

IR (KBr disc,u $cm^{-1}$): 1710 (vs. sharp, COO); 1620 (sh), 1608 (vs, sharp; C=N, C=O and C=C—N coordinated).

$^1$H NMR ($CDCl_3$): d 7.45–6.50 (m, 11H; aromatic $C_6H_4$, HC=N, HC=O, NCH=C, aromatic $C_6H_4$); 4.05 (s, br, 2H, $CH_2$—OCO); 3.76 (s, br, 2H, $CH_2$O-Ph); 3.34 (s, br, 4H, $CH_2$—N=CH, $CH_2$—NH); 2.51–1.50 (br, several signals, $CH_2$—CH—OCO, $CH_2$—CH—OCO); $CH_2$—$CH_2$—O, $CH_2$—$CH_2$—O); 1.33 (m, 16H, $(CH_2)_8$).

What is claimed is:

1. A set of compounds defined by formulas 1 and 2:

Formula 1

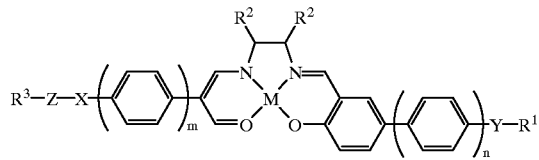

Formula 2

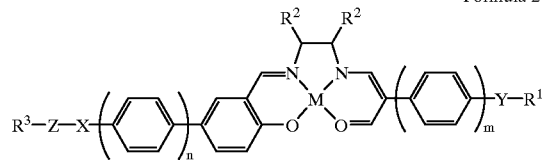

where:

X=—OOC—, —COO—, —CO—, —O—, —S—, alkyne, σ-bond;

Y=—OOC—, —COO—, —CO—, —O—, —S—, alkyne, σ-bond;

Z=alkyl spacer;

$R^1$=H or alkyl, $R^2$=H, F, $CH_3$;

$R^3$=alkyl, alkenyl, alkynyl, HOH,

$CH_2$=CH—COO (acrylate), $CH_2$=CH($CH_3$)CHOO (methacrylate); and m=0, 1; n=0, 1, 2; M is a transition metal;

wherein alkyl, alkenyl, and alkynyl have up to 11 carbon atoms.

2. The compound of claim having a formula:

Formula 3

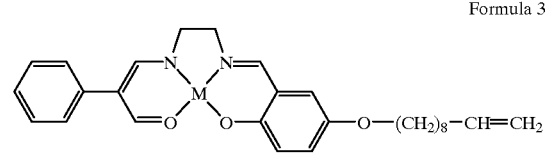

where M=Ni or Cu.

3. A compound having a formula:

Formula 4

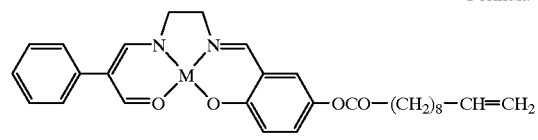

where M=Ni, Cu or VO.

4. A compound having a formula:

formula 5

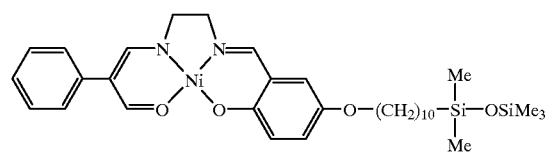

where M=Ni or Cu.

5. The compound of claim 1 having a formula:

formula 6

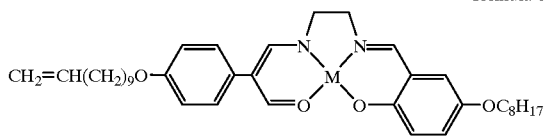

where M=Ni or Cu.

6. A compound having a formula:

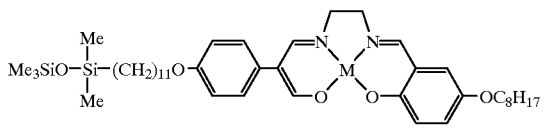

formula 7 where M=Ni or Cu.

7. A method of synthesizing oligomeric and polymeric liquid crystalline materials containing a coordinated transitional metal center in the mesogenic side chain, the method comprising the steps of:

(i) activating a non-symmetrical monomer towards polymerization; and (ii) polymerizing the monomer;

wherein only one moiety is activated towards polymerization and wherein the monomer has the formula:

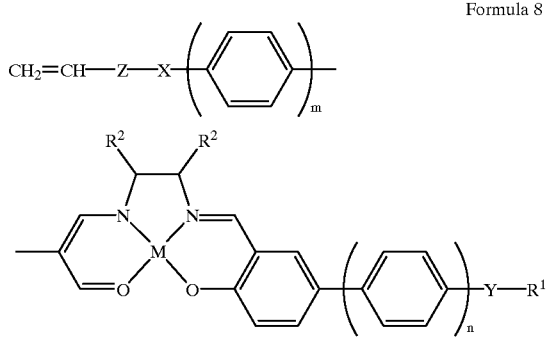

Formula 8 or the formula:

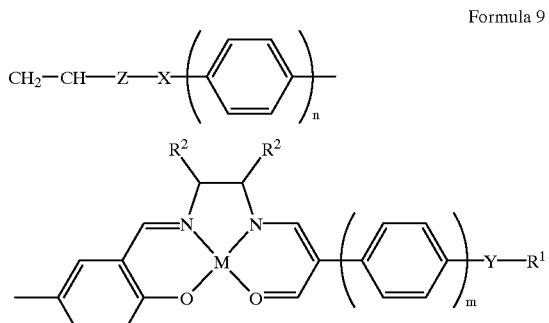

Formula 9 wherein

X and Y are independently selected from —OCO—, —COO—, —CO—, —O—, —S—, alkyne, σ-bond;

Z=alkyl spacer;

$R^1$=H or alkyl, $R^2$=H, F, $CH_3$;

m=0, 1; n=0, 1, 2;

M is a transition metal and the aromatic rings defined by m and n may possess fluoro substituents or may be replaced by heterocyclic or by saturated alicyclic rings; and wherein alkyl has up to 11 carbon atoms.

8. The method according to claim 7 wherein the monomer has the formula:

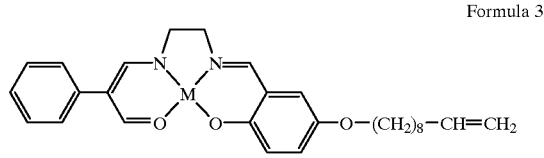

Formula 3

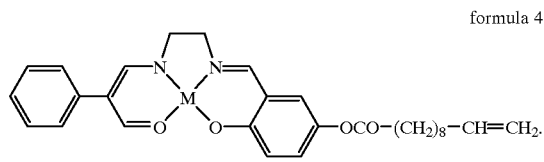

formula 4

9. A method of synthesizing oligomeric and polymeric liquid crystalline materials containing a co-ordinated transitional metal center in the mesogenic side chain, the method comprising the following steps:

(i) activating a non-symmetrical monomer towards polymerization; and (ii) polymerizing the monomer;

wherein only one moiety is activated towards polymerization and wherein the monomer has the general formula:

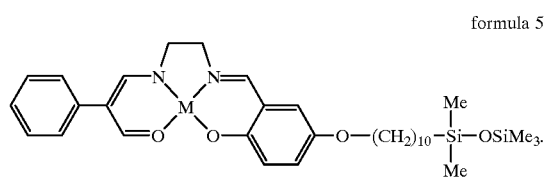

formula 5

10. An oligomeric or polymeric liquid crystalline material, containing a coordinated transition metal center in the mesogenic side chain, having a repeat unit represented by formula 10 or 11:

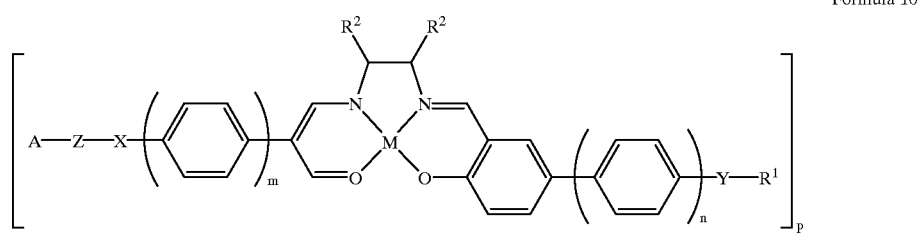

Formula 10

-continued

Formula 11

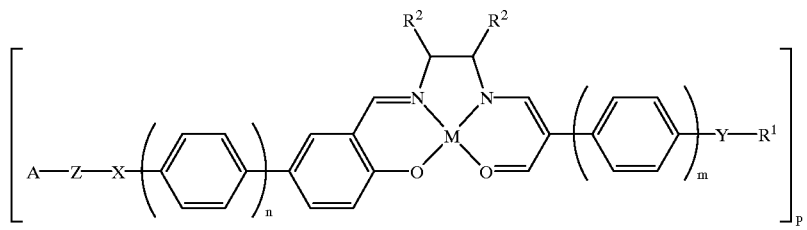

where

X=—OOC—, —COO—, —CO—, —O—, —S—, alkyne, σ-bond;

Y=—OOC—, —COO—, —CO—, —O—, —S—, alkyne, σ-bond;

Z=alkyl spacer;

$R^1$=H or alkyl, $R^2$=H, F, $CH_3$;

m=0, 1; n=0, 1, 2;

wherein alkyl has up to 11 carbon atoms;

M is a transition metal;

P represents the degree of polymerization and

A is an oligomeric or polymeric modifier:

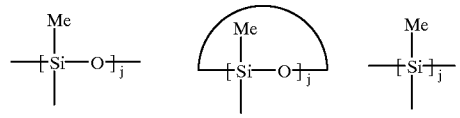

-continued

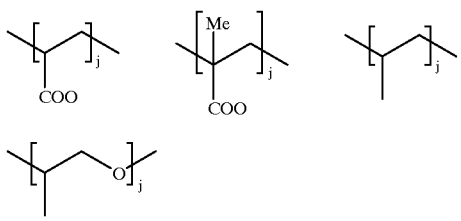

or $([SiO_{3/2}][SiR_2^4O]_b)_a$ wherein a=integer from 4 to 18;

b=integer from 0 to 10 and j=degree of polyemerization; and $R^4$=an alkyl group.

11. A liquid crystalline material having a formula 12

Formula 12
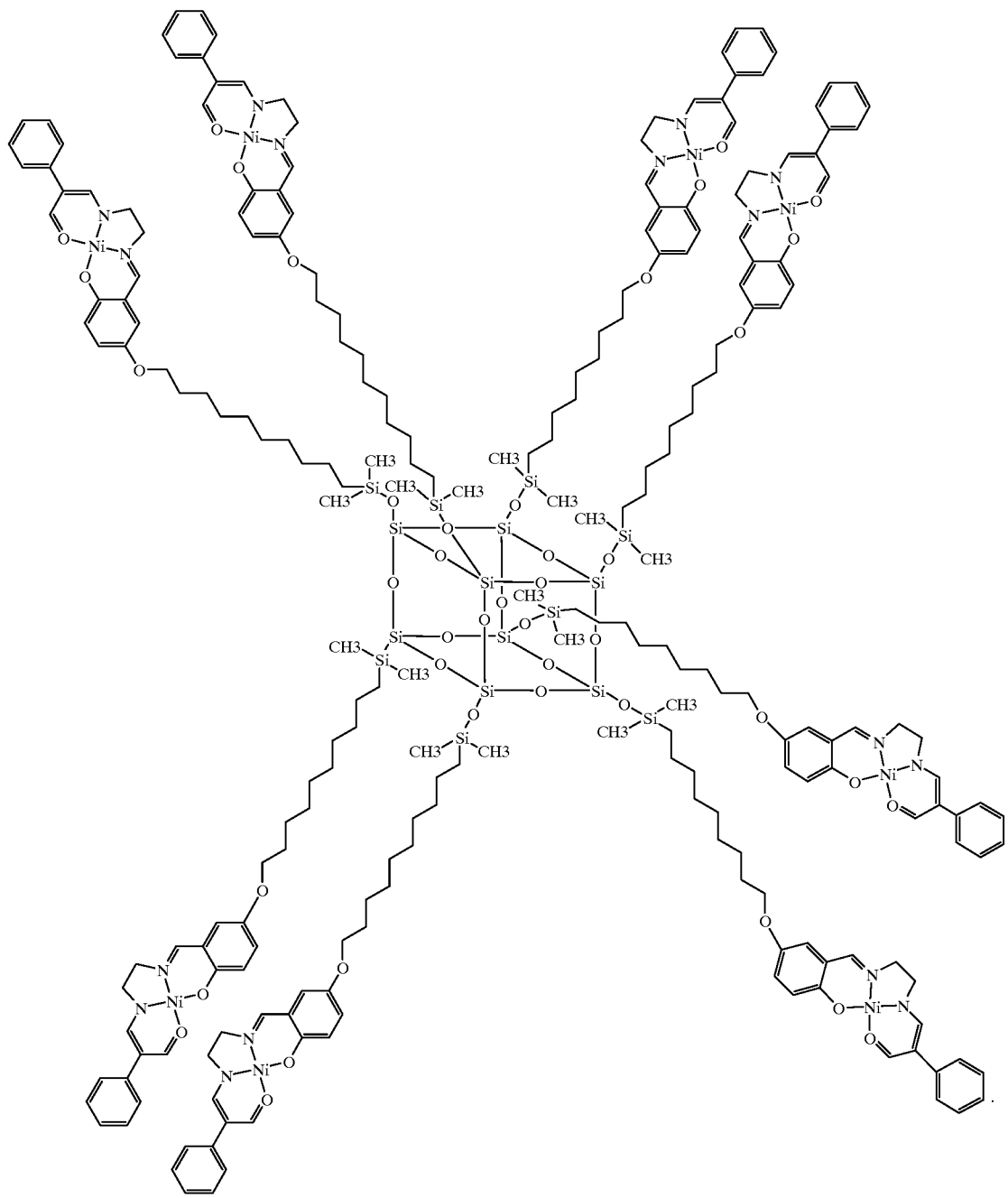
12. The liquid crystalline material having a formula 13

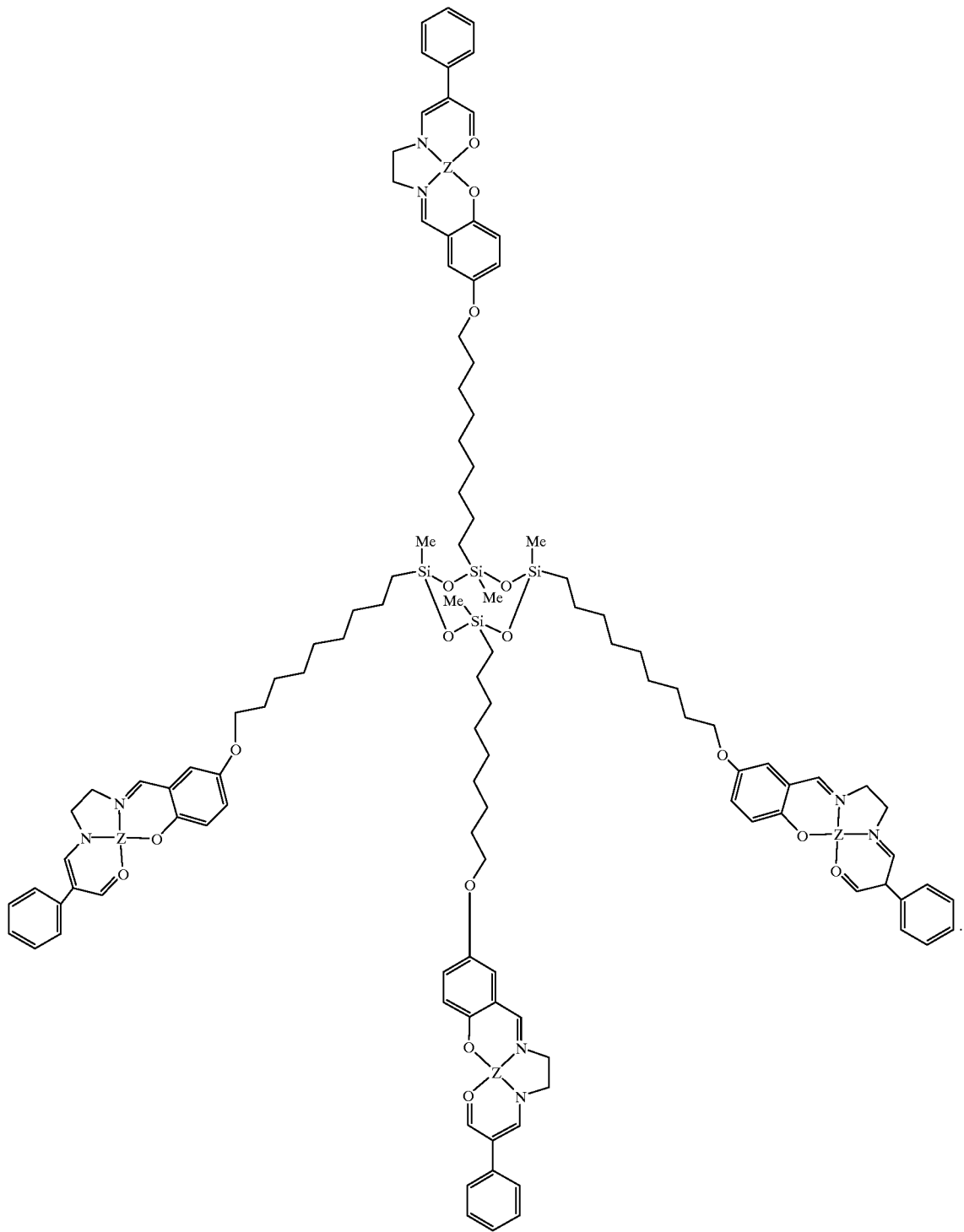
Formula 13
13. A dimethylsiloxy liquid crystalline material of Formula 14

Formula 14

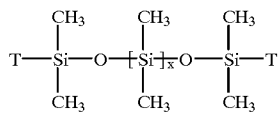

wherein x is an integer greater than, or equal to, 0 and T is a group having a formula 15 or 16 below Formula 15

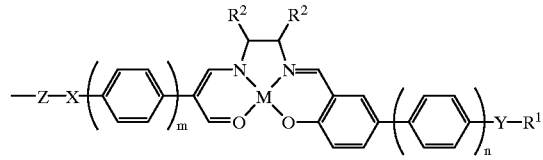

Formula 16

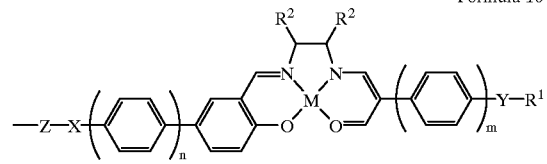

where:
- X=—OOC—, —COO—, —CO—, —O—, —S—, alkyne, σ-bond;
- Y=—OOC—, —COO—, —CO—, —O—, —S—, alkyne, σ-bond;
- Z=alkyl spacer;
- $R^1$=H or alkyl($C_kH_{2k+1}$);
- $R^2$=H, F, $CH_3$;
- m=0, 1; n=0, 1, 2;
- wherein alkyl has up to 11 carbon atoms; and M is a transition metal.

14. A trimethylsiloxy-poly(dimethylsiloxy) liquid crystalline material having a formula 17

Formula 17

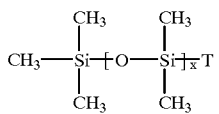

wherein x is an integer greater than, or equal to, 1 and T is a group having a formula:

Formula 15

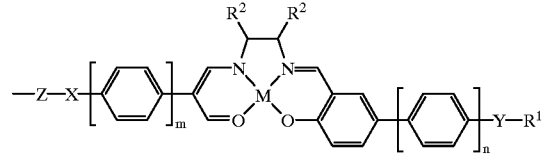

Formula 16

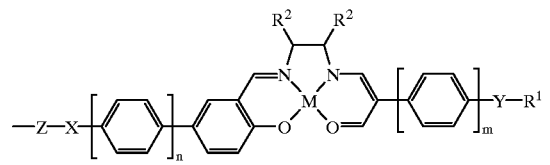

where
- X=—OOC—, —COO—, —CO—, —O—, —S—, alkyne, σ-bond;
- Y=—OOC—, —COO—, —CO—, —O—, —S—, alkyne, σ-bond;
- Z=alkyl spacer;
- $R^1$=H or alkyl,
- $R^2$=H, F, $CH_3$;
- m=0, 1; n=0, 1, 2;
- wherein alkyl has up to 11 carbon atoms; and M is a transition metal.

* * * * *